(12) United States Patent
Draghia-Akli et al.

(10) Patent No.: US 8,962,818 B2
(45) Date of Patent: Feb. 24, 2015

(54) COMPOSITIONS COMPRISING GHRH AND GNRH AND METHODS OF USING THE SAME

(75) Inventors: Ruxandra Draghia-Akli, Brussels (BE); Amir Khan, Blue Bell, PA (US); Patricia Brown, Magnolia, TX (US)

(73) Assignee: VGX Pharmaceuticals, Inc., Plymouth Meeting, PA (US)

( * ) Notice: Subject to any disclaimer, the term of this patent is extended or adjusted under 35 U.S.C. 154(b) by 703 days.

(21) Appl. No.: 12/920,545

(22) PCT Filed: Mar. 6, 2009

(86) PCT No.: PCT/US2009/036379
§ 371 (c)(1),
(2), (4) Date: Oct. 18, 2010

(87) PCT Pub. No.: WO2009/111727
PCT Pub. Date: Sep. 11, 2009

(65) Prior Publication Data
US 2011/0034544 A1    Feb. 10, 2011

Related U.S. Application Data

(60) Provisional application No. 61/034,473, filed on Mar. 6, 2008.

(51) Int. Cl.
*A61K 38/00* (2006.01)
*A61K 38/09* (2006.01)
*A61K 38/25* (2006.01)
*A61K 48/00* (2006.01)

(52) U.S. Cl.
CPC ............... *A61K 38/09* (2013.01); *A61K 38/25* (2013.01); *A61K 48/0016* (2013.01); *A61K 48/005* (2013.01)
USPC ..................................... 536/23.4; 424/78.08

(58) Field of Classification Search
None
See application file for complete search history.

(56) References Cited

U.S. PATENT DOCUMENTS 6,387,695 B1    5/2002    Evans et al.
7,517,863 B2    4/2009    Draghia-Akli et al.

OTHER PUBLICATIONS

Storer. Evaluation of a Plasmid Delivery System for Production of GnRH and GHRH in the Horse and Goat. Ph.D. Dissertation at Louisiana State University. Baton Rouge, LA. Dec 2006. p. 19-20,23,33-34.
UniProtKB P01287 GHRH. Jul. 12, 1986. sequence P01287-1.
UniProtKB P49921 GnRH-1. Oct. 1, 1996 sequence P49921-1.
Storer, et al. "Evaluation of Plasmid Delivery by Electroporation as a Means of Increasing Gonadotropin-Releasing Hormone Production in Stallions" Journal of Equine Veterinary Science vol. 28, No. 3 (2008) pp. 149-155.

*Primary Examiner* — Anand Desai
(74) *Attorney, Agent, or Firm* — Thomas Kim

(57) ABSTRACT

Compositions and kits comprising a nucleotide sequence that encodes GHRH and a nucleotide sequence that encodes GnRH and compositions and kits comprising a GHRH protein and GnRH protein are disclosed. Use of such compositions and kits in methods of enhancing fertility in mammals comprising the step of administering said compositions to the mammal are disclosed.

8 Claims, 9 Drawing Sheets

COMPOSITIONS COMPRISING GHRH AND GNRH AND METHODS OF USING THE SAME

CROSS REFERENCE TO RELATED APPLICATION

This application is a 371 National stage entry of International Application No. PCT/US2009/036379, filed Mar. 6, 2009, and claims the benefit of U.S. Provisional Application No. 61/034,473, filed Mar. 6, 2008, the contents of which are incorporated herein by reference.

FIELD OF THE INVENTION

The invention relates to compositions that comprise nucleic acid molecules that encode growth hormone releasing hormone (GHRH) and gonadotropin releasing hormone (GnRH) and their use to improve mammalian fertility.

BACKGROUND OF THE INVENTION

Growth hormone (GH) and insulin-like growth factor-I (IGF-I) have been shown to be important for fertility, especially in GH-deficient individual that display a lower fertility rate. Growth hormone deficiency or insufficiency can cause a delay in the onset of puberty, unless treated with synthetic GH. It is thought that GH affects the ovary during puberty both indirectly through the gonadotropins and IGF-I and directly through its effect on steroidogenesis. The GH axis is activated by small increases in circulating estrogens, which initiate large increases in GH during puberty. The reproductive function of the female is also affected by GH. GH acts on the ovary affecting gametogenesis and steroidogenesis. GH receptor mRNA and protein have been found in the ovarian cell, which suggests that direct action of GH provides an important modulatory effect on gonadotropin's dependent and independent functions. It also affects the maturation of the follicle and gamete, and thereby plays a facilitatory role in fertility. The majority of women with GH-deficiency, but not all, require assisted reproductive technologies to induce ovulation.

Overexpression of GH also negatively impacts reproduction. Reproduction life span and efficiency are reduced in both sexes, with the severity and frequency of reproductive deficits being related to plasma bGH levels. Most transgenic females expressing high levels of bGH are sterile due to luteal failure. In mouse, overexpression of human GH, which interacts with both GH and PRL receptors, leads to additional endocrine and reproductive abnormalities including stimulation of LH beta mRNA levels and LH secretion, loss of responsiveness to testosterone feedback, overstimulation of mammary glands, enhanced mammary tumorigenesis, and hypertrophy of accessory reproductive glands in males.

In a model of GHRH-KO (Alba, Endocrinology. 2004 September; 145(9):4134-43) male homozygous animals had normal copulatory behavior and fertility. When mated with heterozygous females, no differences in terms of litter size (8.3 pups/litter) or Mendelian ratio for offspring was observed. On the contrary, homozygous females, although maintaining normal fertility, had a consistent reduction in litter size (average, 4.1 pups/litter). All homozygous adult females displayed normal duration of gestation (19-21 d), normal pup retrieval, and normal maternal behavior.

Hormone therapies with protein or peptide hormones, agonists, and antagonists are short-lived in vivo and have required frequent injections or depot delivery to elicit long-term effects on physiologic systems. In many instances, protein hormone therapy can be inefficient and labor intensive. This is due in part to the cost, availability, and pharmacokinetics of many protein preparation.

Recently, the ability to transfect DNA into adult mammals has overcome the barriers of impracticality and economic infeasibility associated with long-term protein hormone therapy. Plasmid therapy has evolved over the past decade into a safe approach for delivery of DNA and their gene product in vivo (Prud'homme, Curr Gene Ther. 2006 April; 6(2):243-73). Combining new plasmid delivery technologies with the elucidation of genetic information for domestic mammals could expand the use of this technique in future therapies. Delivery of plasmids by direct intramuscular injection followed by a physical method to enhance plasmid uptake and expression, such as electroporation, has shown to be successful in several species of animals. This approach has been applied in autoimmune and/or inflammatory diseases, DNA vaccination against infectious agents (e.g., hepatitis B virus, human immunodeficiency virus-1) or tumor antigens (e.g., HER-2/neu, carcinoembryonic antigen) (Curcio, Cancer Gene Ther. 2008 February; 15(2):108-14) (Hirao, Vaccine. 2008 Jan. 17; 26(3):440-8).

In various species, GH treatment has been beneficial on numerous physiologic systems. In the normal horse, GH has been evaluated for its effects on the cardiovascular system, the musculoskeletal and immune system, and the reproductive axis. Growth hormone treatment has resulted in increased granulocyte number and musculation in aged mares, increased number of small follicles on the ovaries, and increased accessory sex gland function in stallions. In the horse, plasma GH concentrations can be increased by various secretagogues, feeding, and exercise. Pharmacological doses of GHRH are known to increase GH.

Researchers have yet to examine the effects of chronic GH treatment on many physiologic systems in the horse. Because of its short half-life, the use of GHRH to physiologically stimulate the GH axis was not investigated. Nevertheless, previous work showed that by using optimized plasmid constructs, this technique can be applied to impact long-term hormonal and clinical parameters in normal and pathologic circumstances in large mammals, such as dogs, cows, and pigs, using a low plasmid quantity with the absence of adverse effects (reviewed in Draghia-Akli, Comb Chem High Throughput Screen. 2006 March; 9(3):181-5).

Treatment with gonadotropin releasing hormone (GnRH), the hypothalamic peptide regulating pituitary LH and FSH secretion, and its analogues have shown promise for regulating reproductive traits.

GnRH therapy has shown promise as a treatment for improving gonadotropin and testosterone secretion in these scenarios. Chronic, pulsatile administration of GnRH increases LH and testosterone secretion but is less effective on semen motility in stallions. Pulsatile therapy is, however, impractical due to the labor needed and the long-term nature of the treatment. Long-lasting, potent analogues of GnRH initially increase gonadotropin concentrations but subsequently down-regulate gonadotropin production.

There remains a need for compositions and methods of enhancing fertility in mammals. Also needed are methods of enhancing fertility in normal and subfertile mammals, including such methods that also provide economic benefit, which would allow for prophylactic treatments.

SUMMARY OF THE INVENTION

Aspects of the present invention relate to pharmaceutical compositions formulated for administration to a mammal in order to introduce to a cell of the mammal a GHRH product and a GnRH product, wherein the GHRH product comprises a nucleotide sequence that encodes GHRH or a GHRH protein, and the GnRH product comprises a nucleotide sequence that encodes GnRH or a GnRH protein.

Some aspects of the present invention relate to kits comprising a first container comprising a nucleotide sequence that encodes GHRH or a GHRH protein, and a second container comprising a nucleotide sequence that encodes GnRH or a GnRH protein.

Some aspects of the present invention relate to methods of enhancing fertility in mammals. The methods comprise the step of administering to the mammal a nucleotide sequence that encodes GHRH or a GHRH protein, and a nucleotide sequence that encodes GnRH or a GnRH protein. In addition, some embodiments of the methods of enhancing fertility comprise a step of administering by intramuscular injection to said mammal a plasmid that comprises the nucleotide sequence that encodes GHRH and the nucleotide sequence that encodes GnRH. In some embodiments, these aspects comprise a further step of electroporating the muscle tissue after intramuscular injection of the plasmid using constant current.

BRIEF DESCRIPTION OF THE FIGURES

The invention can be more fully understood from the following detailed description and the accompanying drawings, all of which form a part of this application.

DESCRIPTION OF PREFERRED EMBODIMENTS

Figure 1:
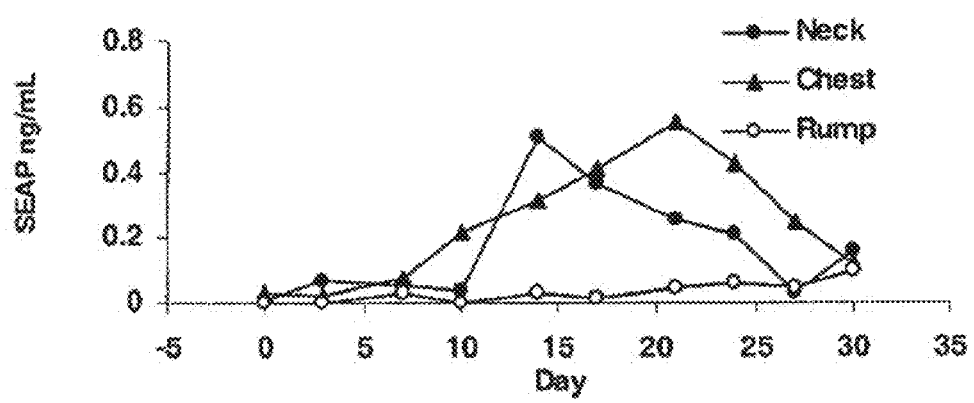
FIG. 1 displays a graph showing the mean plasma concentrations of SEAP for samples collected twice weekly in response to electroporation with pSEAP (time 0) in the neck (splenius), chest (pectoralis), or rump (semitendinosus). Concentrations of SEAP increased over time ($P<0.05$) and were greatest ($P<0.05$) when delivered in the chest. The least significant difference (LSD) for comparison of means is indicated by the vertical bar.

"GHRH" means wild type growth hormone releasing hormone and functional fragments and analogues thereof. Functional fragments of GHRH refer to truncated or incomplete molecules relative to wild type which retain the biological activity of GHRH. Analogues of GHRH refers to proteins having substitutions, deletions and additions relative to the wild type GHRH provided such proteins retain the biological activity of GHRH and are at least 70% homologous, more preferably at least 75% homologous, more preferably at least 80% homologous, more preferably at least 85% homologous, more preferably at least 90% homologous, more preferably at least 95% homologous, more preferably at least 98% homologous, and more preferably at least 99% homologous to wild type GHRH.

"GnRH" means wild type growth hormone releasing hormone and functional fragments and analogues thereof. Functional fragments of GnRH refer to truncated or incomplete molecules relative to wild type which retain the biological activity of GnRH. Analogues of GnRH refers to proteins having substitutions, deletions and additions relative to the wild type GnRH provided such proteins retain the biological activity of GnRH and are at least 70% homologous, more preferably at least 75% homologous, more preferably at least 80% homologous, more preferably at least 85% homologous, more preferably at least 90% homologous, more preferably at least 95% homologous, more preferably at least 98% homologous, and more preferably at least 99% homologous to wild type GnRH.

The terms "percent (%) homologous" and "percentage of sequence identity" as used herein compare two optimally aligned sequences over a comparison window, wherein the portion of the sequence in the comparison window may comprise additions or deletions (i.e. "gaps") as compared to a reference sequence for optimal alignment of the two sequences being compared. The percentage identity is calculated by determining the number of positions at which the identical residue occurs in both sequences to yield the number of matched positions, dividing the number of matched positions by the total number of positions in the window and multiplying the result by 100 to yield the percentage of sequence identity. Total identity is then determined as the average identity over all of the windows that cover the complete query sequence. In some embodiments, computer software packages such as GAP, BESTFIT, BLASTA, FASTA and TFASTA can also be utilized to determine sequence identity.

The term "coding region" as used herein refers to any portion of the DNA sequence that is transcribed into messenger RNA (mRNA) and then translated into a sequence of amino acids characteristic of a specific polypeptide.

The term "delivery" or "delivering" as used herein is defined as a means of introducing a material into a tissue, subject, or cell of any recipient, by means of chemical or biological process, injection, mixing, electroporation, sonoporation, or combination thereof, either under or without pressure.

The terms "nucleic acid expression construct" and "expression vector" are used interchangeably herein and refer to any type of genetic construct comprising a nucleic acid coding sequence operatively linked to regulatory elements required for gene expression. In specific embodiments, the isolated nucleic acid expression construct comprises: a promoter; a nucleotide sequence of interest; and a 3' untranslated region; wherein the promoter, the nucleotide sequence of interest, and the 3' untranslated region are operatively linked; and in vivo expression of the nucleotide sequence of interest is regulated by the promoter.

The term "operatively linked" as used herein refers to elements or structures in a nucleic acid sequence that are linked by operative ability and not physical location. The elements or structures are capable of, or characterized by accomplishing a desired operation. It is recognized by one of ordinary skill in the art that it is not necessary for elements or structures in a nucleic acid sequence to be in a tandem or adjacent order to be operatively linked.

The term "poly-L-glutamate ("LGS")" as used herein refers to a biodegradable polymer of L-glutamic acid that is suitable for use as a vector or adjuvant for DNA transfer into cells with or without electroporation.

The term "post-injection" as used herein refers to a time period following the introduction of a nucleic acid cassette that contains heterologous nucleic acid sequence encoding GHRH or a biological equivalent thereof into the cells of the subject and allowing expression of the encoded gene to occur while the modified cells are within the living organism.

The term "plasmid" as used herein refers generally to a construction comprised of extra-chromosomal genetic material, usually of a circular duplex of DNA that can replicate independently of chromosomal DNA. Plasmids, or fragments thereof, may be used as vectors. Plasmids are double-stranded DNA molecule that occur or are derived from bacteria and (rarely) other microorganisms. However, mitochondrial and chloroplast DNA, yeast killer and other cases are commonly excluded.

The term "plasmid mediated gene supplementation" as used herein refers a method to allow a subject to have prolonged exposure to a therapeutic range of a therapeutic protein by utilizing an isolated nucleic acid expression construct in vivo.

The term "plasmid backbone" as used herein refers to a sequence of DNA that typically contains a bacterial origin of replication, and a bacterial antibiotic selection gene, which are necessary for the specific growth of only the bacteria that are transformed with the proper plasmid. However, there are plasmids, called mini-circles, which lack both the antibiotic resistance gene and the origin of replication (Darquet et al., 1997; Darquet et al., 1999; Soubrier et al., 1999). The use of in vitro amplified expression plasmid DNA (i.e. non-viral expression systems) avoids the risks associated with viral vectors. The non-viral expression systems products generally have low toxicity due to the use of "species-specific" components for gene delivery, which minimizes the risks of immunogenicity generally associated with viral vectors. One aspect of the current invention is that the plasmid backbone does not contain viral nucleotide sequences.

The term "promoter" as used herein refers to a sequence of DNA that directs the transcription of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "replication element" as used herein comprises nucleic acid sequences that will lead to replication of a plasmid in a specified host. One skilled in the art of molecular biology will recognize that the replication element may include, but is not limited to a selectable marker gene promoter, a ribosomal binding site, a selectable marker gene sequence, and a origin of replication.

The term "residual linear plasmid backbone" as used herein comprises any fragment of the plasmid backbone that is left at the end of the process making the nucleic acid expression plasmid linear.

The term "tissue" as used herein refers to a collection of similar cells and the intercellular substances surrounding them. A skilled artisan recognizes that a tissue is an aggregation of similarly specialized cells for the performance of a particular function. For the scope of the present invention, the term tissue does not refer to a cell line, a suspension of cells, or a culture of cells. In a specific embodiment, the tissue is electroporated in vivo. In another embodiment, the tissue is not a plant tissue. A skilled artisan recognizes that there are four basic tissues in the body: 1) epithelium; 2) connective tissues, including blood, bone, and cartilage; 3) muscle tissue; and 4) nerve tissue. In a specific embodiment, the methods and compositions are directed to transfer of linear DNA into a muscle tissue by electroporation.

The term "therapeutic element" as used herein comprises nucleic acid sequences that will lead to an in vivo expression of an encoded gene product. One skilled in the art of molecular biology will recognize that the therapeutic element may include, but is not limited to a promoter sequence, a transgene, a poly A sequence, or a 3' or 5' UTR.

The term "viral backbone" as used herein refers to a nucleic acid sequence that does not contain a promoter, a gene, and a 3' poly A signal or an untranslated region, but contain elements including, but not limited at site-specific genomic integration Rep and inverted terminal repeats ("ITRs") or the binding site for the tRNA primer for reverse transcription, or a nucleic acid sequence component that induces a viral immunogenicity response when inserted in vivo, allows integration, affects specificity and activity of tissue specific promoters, causes transcriptional silencing or poses safety risks to the subject.

The term "constant current" is used herein to define a preferred current, one that is received or experienced by a tissue, or cells defining said tissue, at a constant amperage over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

The term "feedback" or "current feedback" is used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. Preferably, the feedback is accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. In some embodiments, the feedback loop is instantaneous as it is an analog closed-loop feedback.

The terms "electroporation," "electro-permeabilization," or "electro-kinetic enhancement" ("EP"), as used interchangeably herein, refer to the use of a transmembrane electric field pulse to induce microscopic pathways (pores) in a bio-membrane; their presence allows biomolecules such as plasmids, oligonucleotides, siRNA, drugs, ions, and/or water to pass from one side of the cellular membrane to the other.

The term "decentralized current" is used herein to define the pattern of electrical currents delivered from the various needle electrode arrays of the electroporation devices described herein, wherein the patterns minimize, or preferably eliminate, the occurrence of electroporation related heat stress on any area of tissue being electroporated.

The term "feedback mechanism" as used herein refers to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. The term "impedance" is used herein when discussing the feedback mechanism and can be converted to a current value according to Ohm's law, thus enabling comparisons with the preset current. In a preferred embodiment, the "feedback mechanism" is performed by an analog closed loop circuit.

In some embodiments, there are pharmaceutical compositions formulated for administration to a mammal in order to introduce to a cell of the mammal a GHRH product and a GnRH product, wherein the GHRH product comprises a nucleotide sequence that encodes GHRH or a GHRH protein, and the GnRH product comprises a nucleotide sequence that encodes GnRH or a GnRH protein.

In some embodiments, there are methods of enhancing fertility in mammals. The methods comprise the step of administering to the mammal a nucleotide sequence that encodes GHRH or a GHRH protein, and a nucleotide sequence that encodes GnRH or a GnRH protein.

In some embodiments, the nucleotide sequence that encodes GHRH and the nucleotide sequence that encodes GnRH are equine (horse) sequences, canine (dog) sequences, feline (cat) sequences, porcine (pig) sequences, bovine (cow) sequences, ovine (sheep) sequences, caprine (goat) sequences; or primate sequence including human sequences. Table 1 shows Genbank accession numbers, which are incorporated herein by reference, of GHRH and GnRH sequences.

In some embodiments, the nucleotide sequences that encode GHRH and the nucleotide sequence that encodes GnRH are on one or more DNA molecules. In some embodiments, the nucleotide sequences that encode GHRH and the nucleotide sequence that encodes GnRH are on the same DNA plasmid molecule. In some embodiments, the nucleotide sequences that encode GHRH and the nucleotide sequence that encodes GnRH are on separate plasmid DNA molecule. In some embodiments, the nucleotide sequences that encode GHRH and the nucleotide sequence that encodes GnRH are on the same viral vector genomic nucleic acid molecule. In some embodiments, the nucleotide sequences that encode GHRH and the nucleotide sequence that encodes GnRH are on separate viral vector genomic nucleic acid molecules.

Nucleotide sequences that encode GHRH and GnRH preferably are operably linked to regulatory sequences which are required for expression of the coding sequence in the cells of a mammalian species. Regulatory sequences include promoters, enhancers, other 5' untranslated regions, polyadenylation signals and other 3' untranslated regions.

Examples of promoters include, but are not limited to, skeletal alpha-actin promoter, myosin light chain promoter, cytomegalovirus promoter, and SV40 promoter. In some embodiments, the promoter is tissue specific, such as for example, muscle specific. In some embodiments, the promoter is a synthetic myogenic promoter such as those disclosed in U.S. Pat. No. 6,551,986, which is incorporated herein by reference in its entirety, or non-synthetic myogenic promoter such as those disclosed in U.S. Pat. Nos. 5,374,544 and 5,298,422) which are also incorporated herein by reference in its entirety. In some embodiments, the promoter is an inducible promoter such as SPc5-12, which is disclosed in U.S. Pat. No. 7,241,744, which is also incorporated herein by reference in its entirety.

Additional examples of promoter and/or enhancers can be derived from: Immunoglobulin Heavy Chain, Immunoglobulin Light Chain, T-Cell Receptor, HLA DQ alpha and/or DQ .beta, beta.-Interferon, Interleukin-2, Interleukin-2 Receptor, MHC Class II 5, MHC Class II HLA-Dra beta,-Actin (Kawamoto et al., 1988; Kawamoto et al., 1989), Muscle Creatine Kinase (MCK) (Horlick and Benfield, 1989; Jaynes et al., 1988), Prealbumin (Transthyretin), Elastase I, Metallothionein (MTII) (Inouye et al., 1994; Narum et al., 2001; Skroch et al., 1993), Collagenase, Albumin (Pinkert et al., 1987; Tronche et al., 1989), alpha.-Fetoprotein, gamma-Globin, beta.-Globin (Tronche et al., 1990; Trudel and Costantini, 1987), c-fos, c-HA-ras, Insulin (German et al., 1995; Ohlsson et al., 1991), Neural Cell Adhesion Molecule (NCAM), alpha1-Antitrypsin, H2B (TH2B), Histone, Mouse and/or Type I Collagen, Glucose-Regulated Proteins (GRP94 and GRP78), Rat Growth Hormone (Larsen et al., 1986), Human Serum Amyloid A (SAA), Troponin I (TN I) (Lin et al., 1991; Yutzey and Konieczny, 1992), Platelet-Derived Growth Factor (Pech et al., 1989) (PDGF), Duchenne Muscular Dystrophy (Klamut et al., 1990; Klamut et al., 1996), SV40, Polyoma Retroviruses, Papilloma Virus, Hepatitis B Virus, Human Immunodeficiency Virus, Cytomegalovirus CMV (Boshart et al., 1985; Dorsch-Hasler et al., 1985), Gibbon Ape Leukemia Virus, and Synthetic muscle specific promoters (Draghia-Akli et al., 1999; (c5-12, c1-28 Draghia-Akli et al., 2002; Li et al., 1999).

Examples of Inducer Element may be derived from, for example, MT II Phorbol Ester (TFA), Heavy metals, MMTV (mouse mammary Glucocorticoids tumor virus), beta-Interferon, Poly (rI)x/Poly (rc), Adenovirus 5 E2 E1A, Collagenase, Phorbol Ester (TPA), Stromelysin Phorbol Ester (TPA), SV40, Murine MX Gene, Interferon, Newcastle Disease Virus GRP78 Gene A23187, alpha.-2-Macroglobulin, IL-6, Vimentin Serum, MHC Class I Gene H-2.kappa.b, Interferon HSP70 E1A, SV40 Large T Antigen, Proliferin Phorbol Ester-TPA, Tumor Necrosis Factor alpha, PMA, Thyroid Stimulating Hormone, and Thyroid Hormone alpha Gene.

Examples of polyadenylation signals include, but are not limited to, the SV40 polyadenylation signal, the bovine growth hormone polyadenylation signal and the human growth hormone polyadenylation signal.

Examples of 3' untranslated regions include human growth hormone, bovine growth hormone, SV40, and skeletal alpha actin 3' untranslated regions, human growth hormone 3' UTR, bovine growth hormone 3' UTR.

Examples of viral vectors include but are not limited to adenovirus, SV40 virus, adeno-associated virus, vaccinia virus, and pox virus.

The compositions comprising nucleotide sequences that encodes GHRH and nucleotide sequences that encodes GnRH may be formulated and administered in an amount sufficient to be therapeutically effective, i.e., in a therapeutically effective amount. In some embodiments, the nucleic acid molecules that include the nucleotide sequences that encode GHRH and nucleotide sequences that encode GnRH are formulated in sterile water or in a buffer such as PBS. In some embodiments, the addition, nucleic acid molecules, such as plasmids, are formulated with poly-L-glutamate ("LGS") and/or polyvinylpyrolidone (PVP).

Nucleic acid molecules may be formulated with, or otherwise delivered with, DNA transporters. DNA transporters refer to molecules which bind to DNA vectors and are capable of being taken up by cells. DNA transporters contain a molecular complex capable of non-covalently binding to DNA and efficiently transporting the DNA through the cell membrane. It is preferable that the transporter also transport the DNA through the nuclear membrane. See, e.g., the following applications all of which (including drawings) are hereby incorporated by reference herein: (1) Woo et al., U.S. Pat. No. 6,150,168 entitled: "A DNA Transporter System and Method of Use;" (2) Woo et al., PCT/US93/02725, entitled "A DNA Transporter System and method of Use", filed Mar. 19, 1993; (3) Woo et al., U.S. Pat. No. 6,177,554 "Nucleic Acid Transporter Systems and Methods of Use;" (4) Szoka et al., U.S. Pat. No. 5,955,365 entitled "Self-Assembling Polynucleotide Delivery System;" and (5) Szoka et al., PCT/US93/03406, entitled "Self-Assembling Polynucleotide Delivery System", filed Apr. 5, 1993, each of which is incorporated herein by reference. Another method of delivery involves a DNA transporter system. The DNA transporter system consists of particles containing several elements that are independently and non-covalently bound to DNA. Each element consists of a ligand which recognizes specific receptors or other functional groups such as a protein complexed with a cationic group that binds to DNA. Examples of cations which may be used are spermine, spermine derivatives, histone, cationic peptides and/or polylysine; one element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide described in the Skoka patent cited above.

Nucleic acid molecules may be formulated with lipids. The lipids may form liposomes which are hollow spherical vesicles composed of lipids arranged in unilamellar, bilamellar, or multilamellar fashion and an internal aqueous space for entrapping water soluble compounds, such as DNA, ranging in size from 0.05 to several microns in diameter. Lipids may be useful without forming liposomes. Specific examples include the use of cationic lipids and complexes containing DOPE which interact with DNA and with the membrane of the target cell to facilitate entry of DNA into the cell.

In some embodiments, there are kits comprising a first container comprising a nucleotide sequence that encodes GHRH or a GHRH protein, and a second container comprising a nucleotide sequence that encodes GnRH or a GnRH protein. In some embodiments, a kit has one container of nucleotide sequences encoding GHRH and GnRH, either as separate nucleic acid sequences, each encoding one or other sequence, or as single nucleic acid sequence that encodes both GHRH and GnRH.

In some embodiments, a composition comprises GHRH protein and GnRH protein. Proteins may be produced by well known recombinant methods in for example, bacterial or eukaryotic cells. Examples of eukaryotic cell expression systems include those using yeast cells, insect cells, and mammalian cells such as CHO cells. Proteins may be formulated using standard formulations for injectable proteins. In some embodiments, a composition is provided comprising GHRH protein and GnRH protein. In some embodiments, a kit is provided which includes a first container comprising a composition comprising GHRH protein and a second container comprising GnRH protein.

The compositions and kits may be used in methods of enhancing fertility in mammals. Enhancing fertility generally refers to increasing number or health of offspring or gametes. Examples of characteristics which reflect enhanced fertility include reduced occurrence of sperm head abnormality; improved sperm count; improved litter number/fecundity.

Examples of mammals include: horses, dogs, cats, pigs, cows, sheep, goats, and primates such as humans, chimpanzees, gorillas, baboons, orangutans, and monkeys.

In some embodiments, the mammal when untreated exhibits normal fertility. In some embodiments, the mammal when untreated exhibits abnormal fertility.

The compositions may be administered to the mammal by direct injection, with or without electroporation, particle mediated DNA injection, and use of gene guns such as those using pressurized fluids or mechanical force. Preferably, the compositions are administered to the mammal by injection into the desired tissue, preferably muscle, or skin, and followed by (or concomitantly with) constant-current electroporation in the same desired tissue.

Gene Delivery and in vivo expression: Recently, the delivery of specific genes to somatic tissue in a manner that can correct inborn or acquired deficiencies and imbalances was reported (Herzog et al., 2001; Song et al., 2001; Vilquin et al., 2001). Gene-based drug delivery offers a number of advantages over the administration of recombinant proteins. These advantages include the conservation of native protein structure, improved biological activity, avoidance of systemic toxicities, and avoidance of infectious and toxic impurities. In addition, nucleic acid vector therapy allows for prolonged exposure to the protein in the therapeutic range, because the newly secreted protein is present continuously in the blood circulation.

The primary limitation of using recombinant protein is the limited availability of protein after each administration. Nucleic acid vector therapy using injectable DNA plasmid vectors overcomes this, because a single injection into the patient's skeletal muscle permits physiologic expression for extensive periods of time (WO 99/05300 and WO 01/06988). Injection of the vectors promotes the production of enzymes and hormones in animals in a manner that more closely mimics the natural process. Furthermore, among the non-viral techniques for gene transfer in vivo, the direct injection of plasmid DNA into muscle tissue is simple, inexpensive, and safe.

A DNA plasmid-based expression system is preferred. In such a system, a non-viral gene vector may be composed of a synthetic gene delivery system in addition to the nucleic acid encoding a therapeutic gene product. This allows the risks associated with the use of most viral vectors to be avoided. The non-viral expression vector products generally have low toxicity due to the use of "species-specific" components for gene delivery, which minimizes the risks of immunogenicity generally associated with viral vectors. Additionally, no integration of plasmid sequences into host chromosomes has been reported in vivo to date, so that this type of nucleic acid vector therapy avoids the activation of oncogenes or inactivation of tumor suppressor genes. As episomal systems residing outside the chromosomes, plasmids have defined pharmacokinetics and elimination profiles, leading to a finite duration of gene expression in target tissues.

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, e.g., pectin-degrading enzymes, are employed to render the target recipient cells more susceptible to transformation by electroporation than untreated cells.

Administration by electroporation involves the application of a pulsed electric field to create transient pores in the cellular membrane without causing permanent damage to the cell. It thereby allows for the introduction of exogenous molecules (Smith and Nordstrom, 2000). By adjusting the electrical pulse generated by an electrophoretic system, nucleic acid molecules can travel through passageways or pores in the cell that are created during the procedure. U.S. Pat. No. 5,704,908, which is incorporated herein by reference, describes an electroporation apparatus for delivering molecules to cells at a selected location within a cavity in the body of a patient. These pulse voltage injection devices are also described in U.S. Pat. Nos. 5,439,440 and 5,702,304, and PCT WO 96/12520, 96/12006, 95/19805, and 97/07826 which are each incorporated herein by reference.

Recently, significant progress has been obtained using electroporation to enhance plasmid delivery in vivo. Electroporation has been used very successfully to transfect tumor cells after injection of plasmid (Lucas et al., 2002; Matsubara et al., 2001) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001), and dogs (Fewell et al., 2001) to deliver therapeutic genes that encode for a variety of hormones, cytokines or enzymes. Studies using growth hormone releasing hormone (GHRH) showed that plasmid therapy with electroporation is scalable and represents a promising approach to induce production and regulated secretion of proteins in large animals and humans (Draghia-Akli et al., 1999; Draghia-Akli et al., 2002b).

In addition, plasmid formulated with poly-L-glutamate ("LGS") or polyvinylpyrolidone ("PVP") has been observed to increase plasmid transfection and consequently expression of the desired transgene. The anionic polymer sodium LGS could enhance plasmid uptake at low plasmid concentrations, while reducing any possible tissue damage caused by the procedure. LGS is a stable compound and resistant to relatively high temperatures (Dolnik et al., 1993). LGS has been previously used to increase stability in vaccine preparations (Matsuo et al., 1994) without increasing their immunogenicity. It also has been used as an anti-toxin post-antigen inhalation or exposure to ozone (Fryer and Jacoby, 1993). In addition, plasmid formulated with LGS or polyvinylpyrrolidone ("PVP") has been observed to increase gene transfection and consequently gene expression to up to 10 fold in the skeletal muscle of mice, rats and dogs (Fewell et al., 2001; Mumper et al., 1998). LGS has been used to increase stability of anti-cancer drugs (Li et al., 2000) and as "glue" to close wounds or to prevent bleeding from tissues during wound and tissue repair (Otani et al., 1996; Otani et al., 1998).

Although not wanting to be bound by theory, LGS can increase the transfection of the plasmid during the electroporation process, not only by stabilizing the plasmid DNA, and facilitating the intracellular transport through the membrane pores, but also through an active mechanism. For example, positively charged surface proteins on the cells could complex the negatively charged LGS linked to plasmid DNA through protein-protein interactions. When an electric field is applied, the surface proteins reverse direction and actively internalize the DNA molecules, process that substantially increases the transfection efficiency. Furthermore, LGS will prevent the muscle damage associated with in vivo plasmid delivery (Draghia-Akli et al., 2002a) and will increase plasmid stability in vitro prior to injection.

The underlying phenomenon of electroporation is believed to be the same in all cases, but the exact mechanism responsible for the observed effects has not been elucidated. Although not wanting to be bound by theory, the overt manifestation of the electroporative effect is that cell membranes become transiently permeable to large molecules, after the cells have been exposed to electric pulses. There are conduits through cell walls, which under normal circumstances maintain a resting transmembrane potential of ca. 90 mV by allowing bi-directional ionic migration.

Although not wanting to be bound by theory, electroporation makes use of the same structures, by forcing a high ionic flux through these structures and opening or enlarging the conduits. In prior art, metallic electrodes are placed in contact with tissues and predetermined voltages, proportional to the distance between the electrodes are imposed on them. The protocols used for electroporation are defined in terms of the resulting field intensities, according to the formula E=V/d, where ("E") is the field, ("V") is the imposed voltage and ("d") is the distance between the electrodes.

The electric field intensity E has been a very important value in prior art when formulating electroporation protocols for the delivery of a drug or macromolecule into the cell of the subject. Accordingly, it is possible to calculate any electric field intensity for a variety of protocols by applying a pulse of predetermined voltage that is proportional to the distance between electrodes. However, a caveat is that an electric field can be generated in a tissue with insulated electrodes (i.e. flow of ions is not necessary to create an electric field). Although not wanting to be bound by theory, it is the current that is necessary for successful electroporation not electric field per se.

During electroporation, the heat produced is the product of the inter-electrode impedance, the square of the current, and the pulse duration. Heat is produced during electroporation in tissues and can be derived as the product of the inter-electrode current, voltage and pulse duration. The protocols currently described for electroporation are defined in terms of the resulting field intensities E, which are dependent on short voltage pulses of unknown current. Accordingly, the resistance or heat generated in a tissue cannot be determined, which leads to varied success with different pulsed voltage electroporation protocols with predetermined voltages. The ability to limit heating of cells across electrodes can increase the effectiveness of any given electroporation voltage pulsing protocol. For example, prior art teaches the utilization of an array of six needle electrodes utilizing a predetermined voltage pulse across opposing electrode pairs. This situation sets up a centralized pattern during an electroporation event in an area where congruent and intersecting overlap points develop. Excessive heating of cells and tissue along electroporation path will kill the cells, and limit the effectiveness of the protocol. However, symmetrically arranged needle electrodes without opposing pairs can produce a decentralized pattern during an electroporation event in an area where no congruent electroporation overlap points can develop.

Controlling the current flow between electrodes allows one to determine the relative heating of cells. Thus, it is the current that determines the subsequent effectiveness of any given pulsing protocol and not the voltage across the electrodes. Predetermined voltages do not produce predetermined currents, and prior art does not provide a means to determine the exact dosage of current, which limits the usefulness of the technique. Thus, controlling an maintaining the current in the tissue between two electrodes under a threshold will allow one to vary the pulse conditions, reduce cell heating, create less cell death, and incorporate macromolecules into cells more efficiently when compared to predetermined voltage pulses.

One embodiment of the present invention to overcome the above problem by providing a means to effectively control the dosage of electricity delivered to the cells in the inter-electrode space by precisely controlling the ionic flux that impinges on the conduits in the cell membranes. The precise dosage of electricity to tissues can be calculated as the product of the current level, the pulse length and the number of pulses delivered. Thus, a specific embodiment of the present invention can deliver the electroporative current to a volume of tissue along a plurality of paths without, causing excessive concentration of cumulative current in any one location, thereby avoiding cell death owing to overheating of the tissue.

Although not wanting to be bound by theory, the nature of the voltage pulse to be generated is determine by the nature of tissue, the size of the selected tissue and distance between electrodes. It is desirable that the voltage pulse be as homogenous as possible and of the correct amplitude. Excessive field strength results in the lysis of cells, whereas a low field strength results in reduced efficacy of electroporation. Some electroporation devices utilize the distance between electrodes to calculate the electric field strength and predetermined voltage pulses for electroporation. This reliance on knowing the distance between electrodes is a limitation to the design of electrodes. Because the programmable current pulse controller will determine the impedance in a volume of tissue between two electrodes, the distance between electrodes is not a critical factor for determining the appropriate electrical current pulse. Therefore, an alternative embodiment of a needle electrode array design would be one that is non-symmetrical. In addition, one skilled in the art can imagine any number of suitable symmetrical and non-symmetrical needle electrode arrays that do not deviate from the spirit and scope of the invention. The depth of each individual electrode within an array and in the desired tissue could be varied with comparable results. In addition, multiple injection sites for the macromolecules could be added to the needle electrode array.

In some embodiments, the electroporation is performed using a constant current electroporation device and in vivo electroporation techniques using same, as described in U.S. Pat. No. 7,245,963, which is incorporated herein by reference in its entirety.

U.S. Pat. No. 4,956,288, which is incorporated herein by reference, is directed to methods for preparing recombinant host cells containing high copy number of a foreign DNA by electroporating a population of cells in the presence of the foreign DNA, culturing the cells, and killing the cells having a low copy number of the foreign DNA.

The dosage for DNA administered is a therapeutically effective amount and varies depending upon known factors such as the pharmacodynamic characteristics, mode and route of administration; type of animal; age of the recipient; sex of the recipient; health of the recipient; weight of the recipient; nature and extent of symptoms; kind of concurrent treatment; frequency of treatment; and the effect desired. Appropriate dosages of the nucleic acid molecules to be administered will vary somewhat depending on the individual subject and the condition being treated. The skilled worker will be able to determine appropriate dosages. In some embodiments, dosages of plasmids and other nucleic acid molecules range from 1 µg to 1 gram DNA, preferably 500 µg to 5 mg, more preferably 50 µg to 500 µg, and more preferably 100 µg to 250 µg.

The dosage for protein administered is a therapeutically effective amount and varies depending upon known factors such as the pharmacodynamic characteristics, mode and route of administration; type of animal; age of the recipient; sex of the recipient; health of the recipient; weight of the recipient; nature and extent of symptoms; kind of concurrent treatment; frequency of treatment; and the effect desired. Appropriate dosages of the protein to be administered will vary somewhat depending on the individual subject and the condition being treated. The skilled worker will be able to determine appropriate dosages.

In addition to compositions comprising a nucleotide sequence that encodes GHRH and a nucleotide sequence that encodes GnRH and kits comprising a first container comprising a nucleotide sequence that encodes GHRH and a second container comprising a nucleotide sequence that encodes GnRH, as wells as compositions comprising GHRH protein and GnRH protein, and kits comprising a first container comprising GHRH protein and a second container comprising GnRH protein, ands the use of such compositions and kits in methods of enhancing fertility in mammals. It is also contemplated that compositions and kits may comprise protein and nucleic acid molecules. For example, in some embodiments, a composition may comprise a nucleotide sequence that encodes GHRH and a nucleotide sequence that encodes GnRH as well as GHRH protein and GnRH protein. In some embodiments, a composition may comprise a nucleotide sequence that encodes GHRH and a nucleotide sequence that encodes GnRH, and additionally GHRH protein. In some embodiments, a composition may comprise a nucleotide sequence that encodes GHRH and a nucleotide sequence that encodes GnRH, and additionally GnRH protein. In some embodiments, a composition may comprise a nucleotide sequence that encodes GHRH, and additionally GHRH protein and GnRH protein. In some embodiments, a composition may comprise a nucleotide sequence that encodes GHRH, and additionally GnRH protein. In some embodiments, a composition may comprise a nucleotide sequence that encodes GnRH, and additionally GHRH protein and GnRH protein. In some embodiments, a composition may comprise a nucleotide sequence that encodes GnRH, and additionally GHRH protein. In some embodiments, a composition may comprise a nucleotide sequence that encodes GHRH and a nucleotide sequence that encodes GnRH, and additionally GHRH protein and GnRH protein. Similarly, kits may be provided which comprise containers which comprise various combinations. The essential element of the kits is that they each comprise one container that comprises a nucleotide sequence that encodes GHRH and/or GHRH protein and a second container that comprises a nucleotide sequence that encodes GnRH and/or GnRH. Some kits have a container and nucleic acid sequence encoding both GHRH and GnRH or a mixture of two nucleotide sequences that encode GHRH and GnRH, respectively.

TABLE I

Available GenBank Accession Numbers for GHRH and GnRH

| Species | GHRH | GnRH |
| --- | --- | --- |
| Horse | XM_001499576.1 | |
| Pig | U90275.1 | NM_214274.1 |
| Mouse | NM_010285.2 | NM_008145.1 |
| Mouse | | BC116897.1 |
| Sheep | EF601976.1 | U02517.1 |
| Goat | P63293 | |
| Human | NM_021081 | NM_001083111 |
| Human | P01286 | NM_001501.1 |
| | | NP_000816 |
| Chimpanzee | XM_525318.2 | |
| Chicken | NM_001040464 | |
| Rat | U10156.1 | |
| Cow | NM_178325.1 | NM_001078137.1 |
| Synthetic Cat | CS402511.1 | |
| Synthetic Cow | CS029897.1 | |

EXAMPLE

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Plasmid Preparation

The plasmid designed for this experiment pGnRH (SEQ ID NO: 1, see below) which contains an encoding sequence set forth as SEQ ID NO: 2, which encodes the first 33 amino acids of porcine GnRH having the sequence set forth as SEQ ID NO: 3; GnRH is described in Weesner G D, et al., Life Sci. 1997; 61:1643-1649) was generated by molecular biology techniques from pGHRH (SEQ ID NO: 4, see below) which encodes a porcine GHRH having sequence as that set forth as SEQ ID NO: 5. pGHRH is a muscle-specific plasmid expressing porcine GHRH provided by VGX Pharmaceuticals, The Woodlands, Tex.

```
(GnRH-insert sequence)
                                          SEQ ID NO: 2
  1 CCATGGAGCC AATTCCGAAA CTTCTAGCCG GACTTCTGCT

GCTGACTCTG TGTGTAGTGG

61 GCTGCTCCAG CAAACACTGG TCCTATGGAT TGCGCCCTGG

ATAATGAAAG CTT

SEQ ID NO: 3
MEPIPKLLAGLLLLTLCVVGCSSQHWSYGLRPG

SEQ ID NO: 5
YADAIFTNSYRKVLGQLSARKLLQDIMSRQQGERNQEQGA
```

The plasmid was reconstructed to replace the existing GHRH cDNA sequence with the cDNA encoding GnRH by enzymatic cleavage at the 5' Nco 1 and 3' Hind III sites. A new cDNA insert was constructed for alternative expression of GnRH based on the porcine gene for GnRH. The constructed insert includes bases 1 through 99 of the porcine GnRH cDNA modified to include an Nco I restriction site at the 5' end and two 3' stop codons in conjunction with a Hind III restriction site. The complete cDNA insert was generated by PCR from two overlapping primer templates [5'-CCATG-GAGCCAATTCCGAAACTTCTAGCCG-GACTTCTGCTGCTG ACTCTGTGTGTAGTGGGCTGC-3' (65 bp) (SEQ ID NO: 6) and 5'-AAGCTTTCATTATCCAGGGCGCAATC-CATAGGACCAGTGTTGGCTGGA GCAGCCCACTACACACAGAGT-3' (69 bp) (SEQ ID NO: 7)] and extended with primers designed for annealing at the generated 5' and 3' ends [5'-CCATGGAGCCAATTC-CGAAA-3' (20 bp) (SEQ ID NO: 8) and 5'-AAGCTTTCAT-TATCCAGGGCG-3' (21 bp) (SEQ ID NO:9)]. The resulting PCR product was cloned using the TOPO® XL PCR Cloning Kit (Gibco Invitrogen). Colonies were selected by kanamycin resistance and plasmid DNA was purified via QIAfilter Plasmid Midi Kit (Qiagen Inc., Valencia, Calif.). The sequence of the purified DNA was then verified by PCR by personnel in the Division of Biotechnology and Molecular Medicine, Louisiana State University School of Veterinary Medicine. Both the TOPO-XL vector and the pGHRH plasmid were simultaneously double-digested with restriction endonucleases Nco I and Hind in (Gibco Invitrogen) for 24 h at 37° C. The digested plasmid and insert products were then separated by agarose gel electrophoresis and purified with the PureLink™ Gel Extraction Kit (Gibco Invitrogen). The products were then ligated using the DNA Ligation Kit Ver. 1 (Takara Minis Bio Inc., Madison, Wis.)—The resulting plasmid was transfected into a DH alpha *E. coli* cell line and selected based on kanamycin resistance. Plasmid DNA was purified from resulting colonies with QIAfilter Plasmid Midi Kit (Qiagen) and the sequence verified by PCR. Select colonies were grown up and plasmid DNA was purified with EndoFree Plasmid Giga Kit (Qiagen).

Example 2

Transfection of Mouse Myoblast Cells

Mouse myoblast cells (Sol8) obtained from the American Type Culture Collection (Manassas, Va.; CRL-2174) were transfected with GnRH plasmid. Prior to transfection, cells were grown to 70 to 80% confluency in Dulbecco's modified Eagle's medium (DMEM; Sigma, St. Louis, Mo.) supplemented with 20% fetal bovine serum (Gibco Invitrogen) and 1% penicillin-streptomycin (Gibco Invitrogen) at 37° C. in a humidified environment of 5% $CO_2$ and 95% air. At 80% confluence, media was replaced with Dulbecco's modified Eagle's medium supplemented with 2% heat-inactivated horse serum (Gibco Invitrogen) and 1% penicillin-streptomycin (Gibco Invitrogen). Cells were then transfected with 4 μg of pGnRH (n=4), or no DNA (n=1) via Fugene 6 Transfection Reagent (Roche Applied Sciences, Indianapolis, Ind.). Transfected cells were incubated for 72 h at 37° C. in a humidified environment 5% $CO_2$ and 95% air. Media was collected at 72 h, and GnRH expression was verified by radioimmunoassay (RIA) of culture media for GnRH.

Example 3

Assessment of Muscle Groups of Horse for Plasmid Delivery

Nine light-horse geldings, 5 to 15 yr of age, weighing between 500 and 600 kg having body condition scores (BCS) of between 6 to 8, were maintained on native grass pasture with supplemental grass hay as needed to maintain body condition. On day 0, the animals were randomly assigned to three groups to receive the SEAP-expressing plasmid (pSEAP having nucleotide sequence as that set forth as SEQ ID NO: 10, see below, into one of 3 unique muscle groups: splenius (neck), pectoralis (chest), and semitendinosus (rump). In preparation for injection and electroporation of the plasmid, horses were first sedated with 1.1 mg/kg of xylazine and 0.02 mg/kg of butorphanol administered intravenously; the delivery site was then clipped and sanitized with chlorahexadine. A total quantity of 2 mg of DNA in 2 mL water for injection was formulated with 0.1% LGS (poly-L-glutamate) and delivered into the select muscle site. The injection was followed by electroporation using a constant current technique. Briefly, eight seconds after plasmid injection, a constant current was delivered at 0.5 Amps, 3 pulses, 52 msec/pulse, with 1 sec interval between pulses using the CELLECTRA™ electroporation device (VGX Pharmaceuticals, Blue Bell, Pa.). Jugular blood samples were collected via venipuncture on day 0, prior to treatment, and on days 3, 7, 10, 14, 17, 21, 24, 27, and 30 after treatment. Blood samples were immediately centrifuged (1,600×g at 5° C. for 15 min) and plasma was harvested and frozen at −15° C. until assay. Plasma from daily samples was analyzed for SEAP by [chemiluminescent assay (Phospha-Light System, Applied Biosystems, Bedford, Mass.).

Visual appraisals of the electroporation sites were conducted in both experiments. No noticeable swelling was detected beyond 24 h after injection in any of the geldings or stallions. Concentrations of SEAP increased (P<0.01) in jugular plasma after electroporation of the pSEAP into all three muscle sites. The highest circulating SEAP values were detected in animals that received the plasmid injection into the pectoralis muscle (P<0.05) (FIG. 1). This muscle was used for the subsequent experiments.

Example 4

Treatment of Stallions with GHRH

Twelve light-horse stallions, 2 to 24 yr of age, weighing between 500 and 600 kg (BCS of 4 to 6), were paired based on age and weight. Stallions were then randomly allotted so that each treatment was represented within each pair. Each stallion received either intramuscular delivery of pGHRH or pSEAP by injection followed by electroporation (n=6/group). The plasmids were delivered as 2 mg of DNA in 2 mL WFI+0.1% LGS as described in Example 3. Blood samples were collected via jugular venipuncture into a heparinized tube on days 0, 1, 5, 8, 12, 15, 20, 22, and 29 relative to injection for assessment of GHRH and SEAP concentrations. On day 22, all stallions received indwelling jugular catheters for frequent blood sampling to characterize the GH secretory patterns of the 2 groups. Catheters were inserted at −60 min, and blood samples were collected into a heparinized tube at 0, 10, 20, 30, 45, 60, 90, 120, 150 min. Blood samples were immediately centrifuged (1,600×g at 5° C. for 15 min) and plasma was harvested and stored frozen (−15° C.) until assay. Plasma samples were analyzed for SEAP by chemiluminescent assay (Phospha-Light System, Applied Biosystems, Bedford, Mass.). Concentrations of GH and IGF-I were determined by RIA, as previously validated for horse tissues (See Sticker, L S, et. al., J. Anim. Sci. 73:1424-1432 (1995) and Thompson, D L, Jr., et. al., J. Anim. Sci. 70:1201-1207 (1992) for GH and IGF-1 determination, respectively).

Semen Characteristics

Semen was collected from all stallions every other day for 14 days beginning 3 weeks before treatment and then again beginning on day 30 relative to treatment. Semen evaluation was conducted on the last 4 ejaculates from each stallion. Gel volume, gel-free volume, progressive motility, concentration, and general sperm morphology were assessed for each ejaculate. Morphological characteristics evaluated were head, midpiece, and tail abnormalities and proximal and distal droplets. Gel-free semen was fixed in 2% buffered formol-saline and 100 sperm from each ejaculate were analyzed with phase contrast microscopy.

Statistical Analysis

Data from blood collections were analyzed by ANOVA for effects of treatment and treatment by time interactions as a randomized block design with repeated measures using SAS mixed procedure (SAS Institute Inc., Gary, N.C.). Seminal characteristics were analyzed for effects of treatment and treatment by period interactions using SAS mixed procedures. Differences at individual time points were determined when a significant difference (LSD) test when (P<0.05) was detected. Plasma concentrations of SEAP in Experiment 2 were adjusted as percent change from individual pretreatment means to account for individual variation in assay baselines.

Administration of pGHRH

Figure 2:
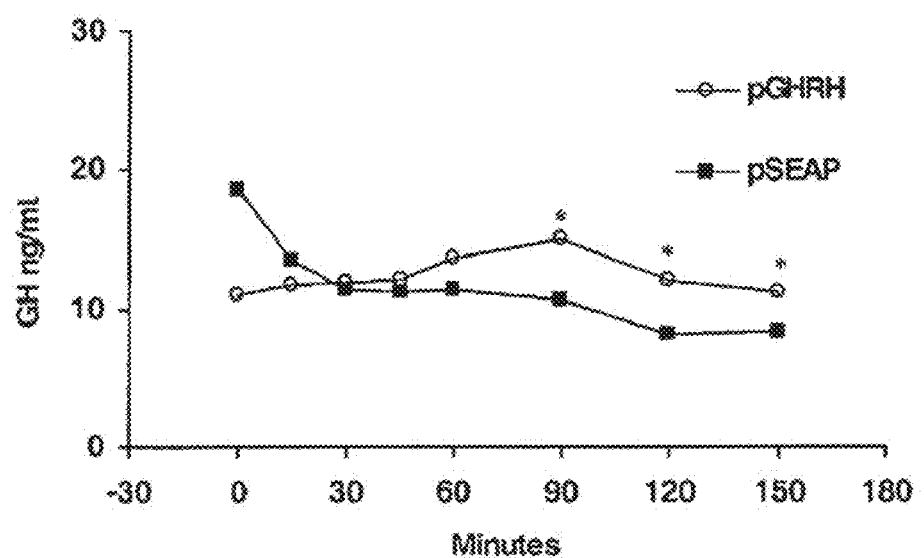
FIG. 2 displays a graph showing mean plasma concentrations of GH in frequent samples collected on d 22 in pGHRH and pSEAP treated stallions. Plasma GH concentrations were increased ($P<0.05$) above control after 90 min. Asterisks indicate differences ($P<0.05$) between means at individual time points.
Figure 3:
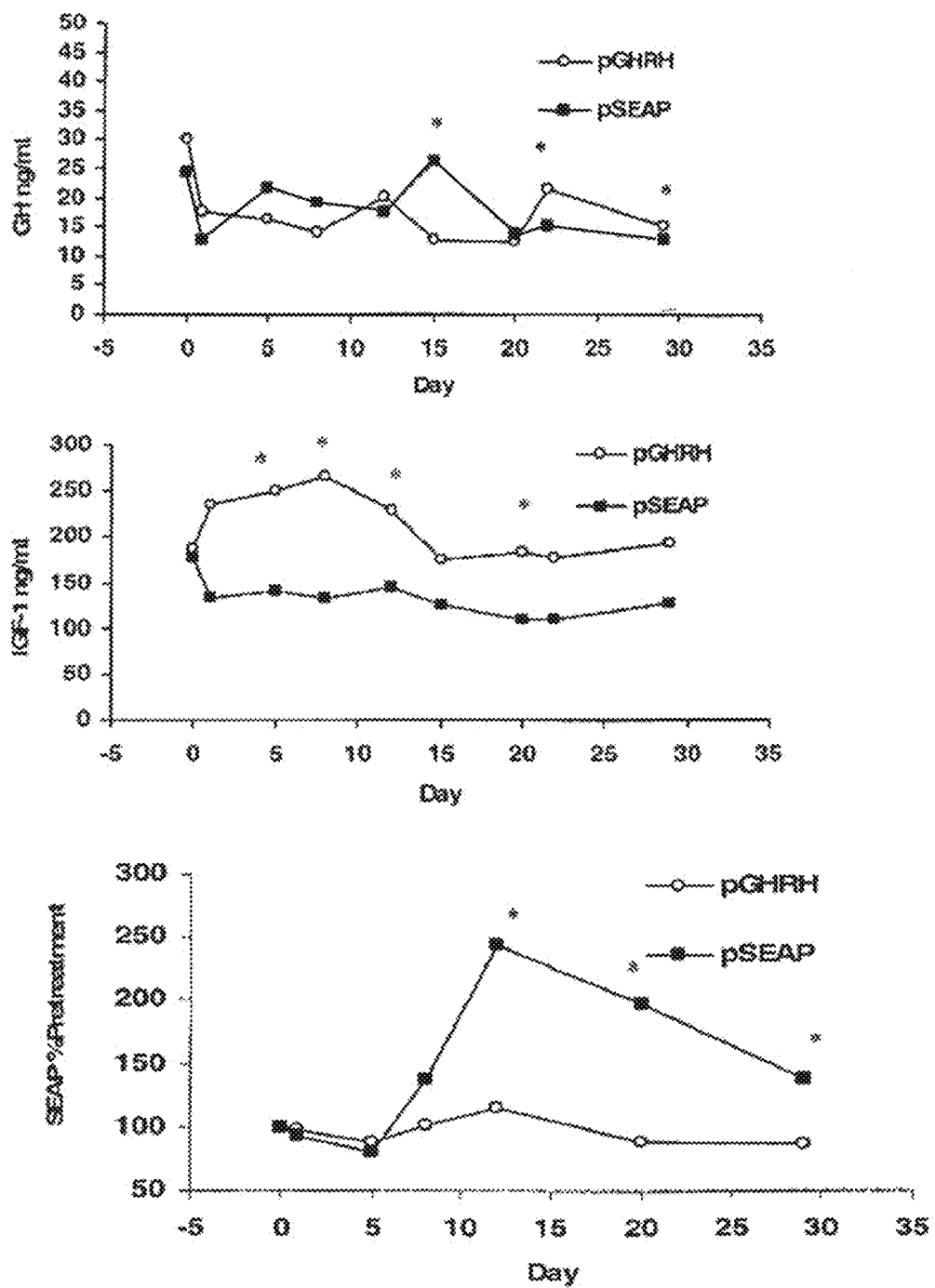
FIG. 3 displays graphs of mean plasma concentrations of: (A) GH, (B) IGF-1, and (C) % of pretreatment SEAP concentrations in samples collected twice weekly in response to electroporation with pGHRH or pSEAP on d 0. Concentrations of GH were not different between treatment groups. Concentrations of IGF-I were increased ($P<0.05$) in pGHRH treated stallions. Concentrations of SEAP increased ($P<0.05$) in pSEAP treated stallions. Asterisks indicate differences ($P<0.05$) between means at individual time points.

Plasma GH concentrations measured by frequent blood sampling on d 22 indicated that stallions treated with the GHRH expressing plasmid maintained basal GH concentrations throughout the blood sampling period, while GH concentrations in pSEAP treated stallions declined (P<0.05; FIG. 2). However, in plasma harvested twice weekly, GH concentrations were not different between treatment groups (FIG. 3A). Concentrations of IGF I were increased (P<0.05) but remained within the physiological range in stallions treated with pGHRH (FIG. 3B). As expected, SEAP concentrations were elevated (P<0.05) in stallions treated with pSEAP (FIG. 3C) but not in stallions receiving the GHRH plasmid.

Figure 4:
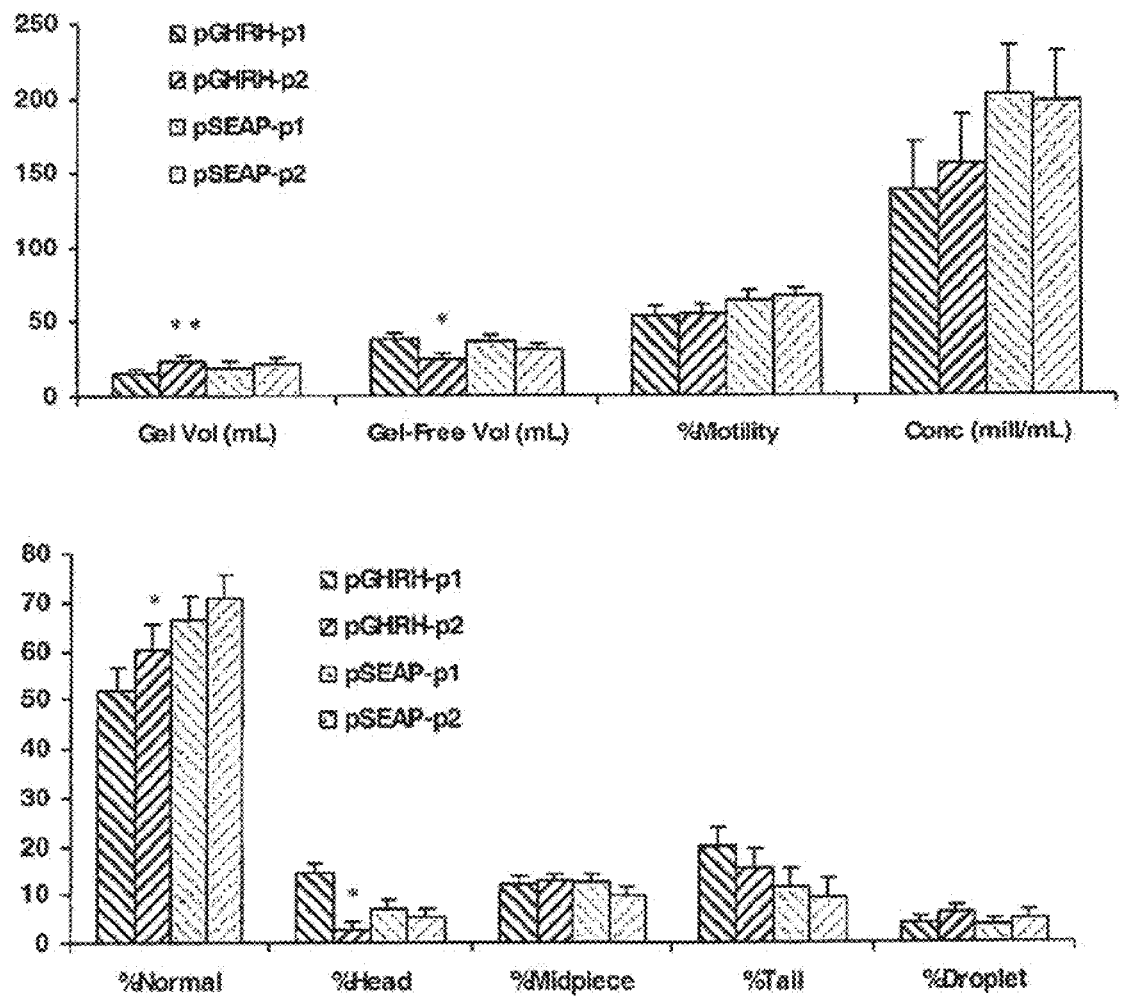
FIG. 4 displays bar graphs of mean seminal parameters for pGHRH and pSEAP treated stallions from ejaculates collected 3 wks prior to treatment (p1) and on d 30 relative to treatment (p2). Stallions treated with pGHRH had decrease ($P<0.05$) in gel-free volume, and increase ($P<0.05$) in percentage of normal spermatozoa, a decrease ($P<0.05$) in percentage of head abnormalities, and a tendency ($P<0.1$) of increased volume of gel. Error bars represent polled standard error, and asterisks indicate differences (*=$P<0.05$ and **=$P<0.1$).

Semen evaluation demonstrated that stallions treated with pGHRH had a decrease (P<0.05) in gel free volume, an increase (P<0.05) in percentage of normal spermatozoa, a decrease (P<0.05) in percentage of head abnormalities, and a tendency (P<0.1) of increased volume of gel (FIG. 4). Other semen characteristics (i.e., concentration of spermatozoa, midpiece abnormalities, and tail abnormalities) did not differ between treatment groups.

Example 5

Treatment of Stallions with GnRH

Ten reproductively sound stallions ranging in age from 2 to 25 yr were used. They were allotted to 3 groups such that average age and weight were similar for the groups. On d 0, stallions m the first group received intramuscular electroporation of 2 mg pGnRH in 2 mL of vehicle (WFI+0.1% LGS; n=3); in the second group, 4 mg of pGnRH in 2 mL vehicle (n=3); and in the third group, 2 mg of pSEAP in 2 mL of vehicle (n=4) as described for Example 3. Preparation and anesthesia of the stallions and injection and electroporation of the plasmids were performed as described previously.

Blood samples were collected from all stallions twice weekly beginning 1 wk before treatment through 6 wk after treatment. On d 21, stallions were fitted with an indwelling jugular catheter. One hour later, all stallions received a challenge Injection of GnRH (0.1 µg/kg of BW, i.v.; Sigma), and blood samples were collected at −20, −10, 0, 10, 20, 30, 60, 90, 120, 150, 180, 210, and 240 min relative to injection to assess the pituitary-gonadal response to GnRH. These blood samples were analyzed for concentrations of GnRH, LH, FSH and testosterone.

Semen collection was conducted daily for 6 d starting 30 d after plasmid injection. Semen evaluation was conducted on the last 3 ejaculates from each stallion. Gel volume, gel-free volume, j progressive motility, concentration, and general sperm morphology were evaluated. Morphological characteristics (head, midpiece, and tail abnormalities and proximal and distal droplets) were assessed in gel-free semen fixed in 2% buffered formol-saline; 100 sperm from each ejaculate were analyzed with phase contrast microscopy.

Blood collected during frequent and daily sampling was immediately centrifuged (1,600×g at 5° C. for 15 min) and plasma was harvested and stored at −15° C. until assay. All samples were analyzed by RIA as previously described for SEAP (Phospha-Light System, Applied Biosystems, Bedford, Mass.), LH, FSH, and testosterone (Diagnostic Systems Laboratories, Webster, Tex.).

Data obtained from blood collections were analyzed for effects of treatment, time, and treatment by time interactions as a randomized block design with repeated measures using SAS mixed procedure (SAS Institute Inc., Cary, N.C.). Seminal characteristics were analyzed for effects of treatment and treatment by period interactions SAS mixed procedures. Differences at individual time points were determined by LSD test when a significant F (P<0.05) was detected. Plasma concentrations of LH, FSH, testosterone and SEAP were adjusted to individual differences from pretreatment means to account for individual variation in resting hormone concentrations. Tissue culture data was analyzed using T-test to compare treatment means.

Figure 5:
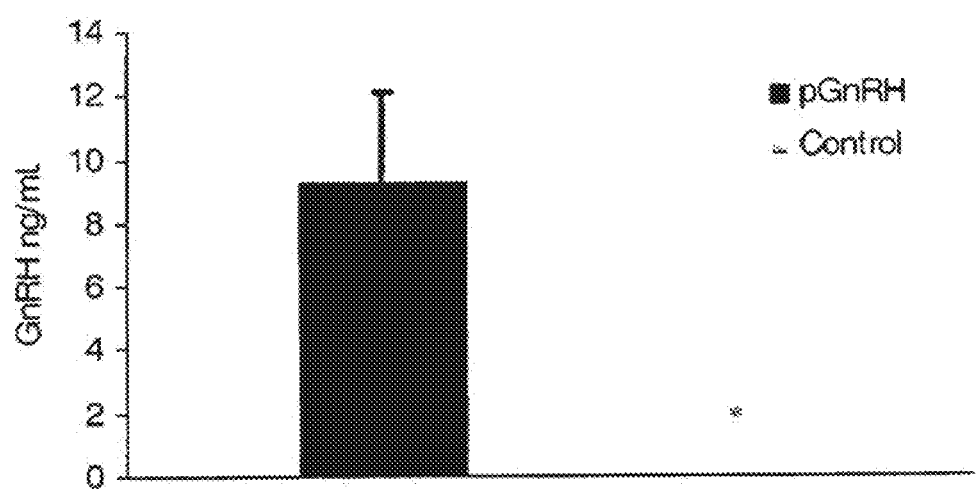
FIG. 5 displays a bar graph of tissue culture concentrations of GnRH in media harvested from Sol8 mouse myoblast cells transfected with pGnRH or no DNA. Cells transfected with pGnRH had increased ($P<0.01$) expression of GnRH. Asterisk indicates GnRH concentration was below detectable levels. Error bar indicates 2 standard deviations from the mean.
Figure 6:
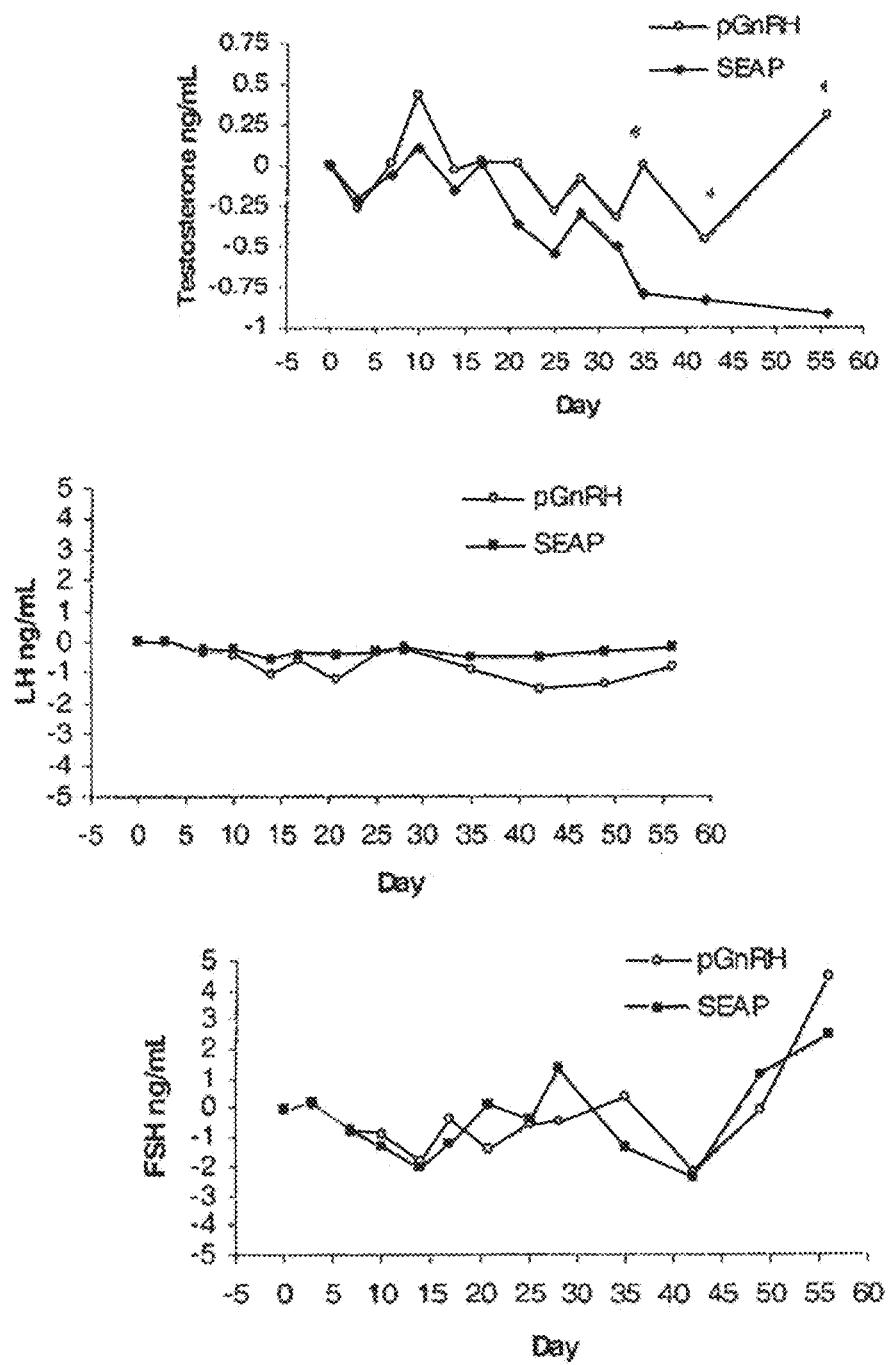
FIG. 6 displays graphs of mean plasma concentrations expressed as individual differences from pretreatment means for testosterone, LH, and FSH in samples collected twice weekly after pGnRH and pSEAP treatment on d 0. Testosterone concentrations increased ($P<0.05$) in pGnRH-treated stallions. Concentrations of LH and FSH were similar between groups. Asterisks indicate differences ($P<0.05$) between means at individual time points.
Figure 7:
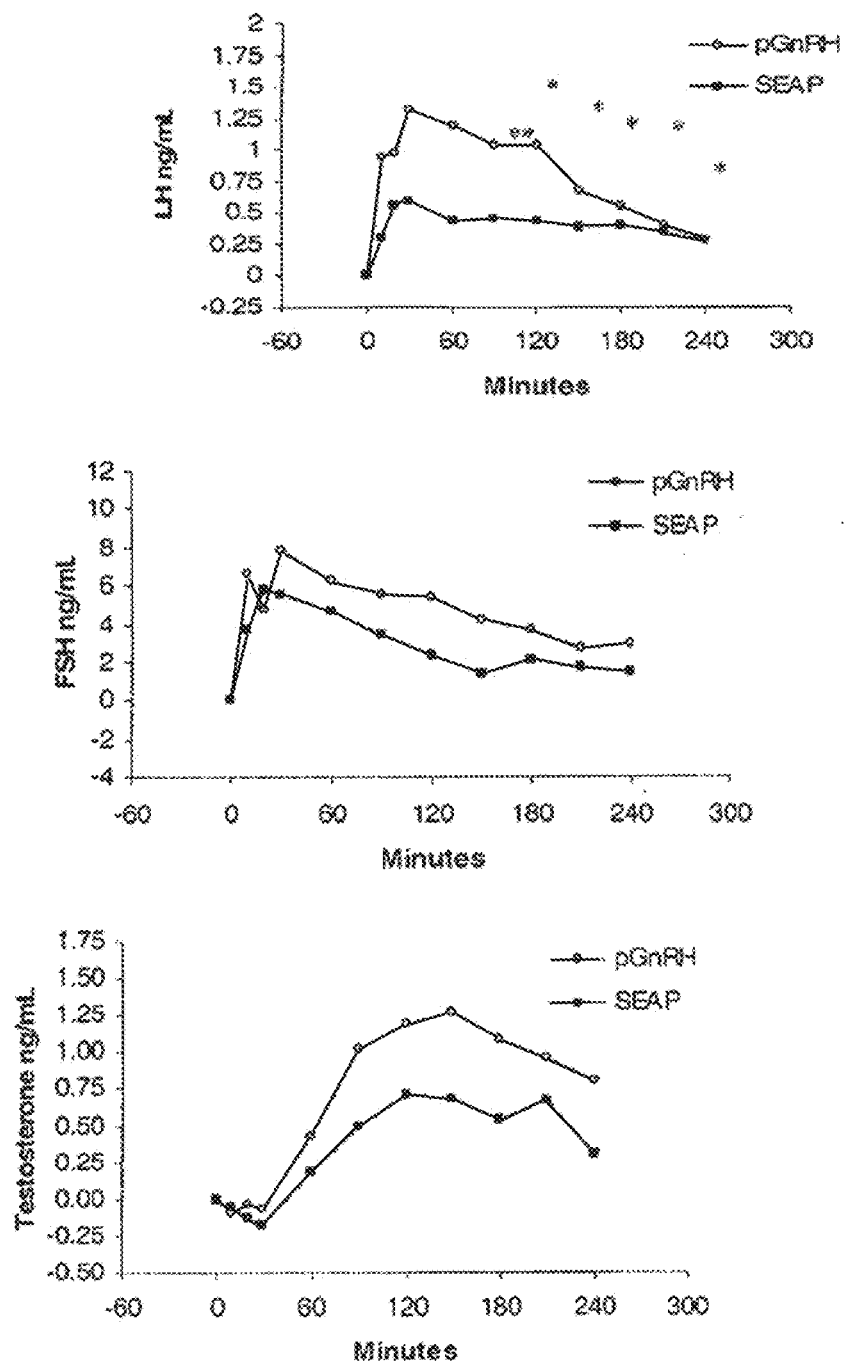
FIG. 7 displays graphs of plasma concentrations expressed as differences from individual pretreatment means for testosterone in pGnRH and pSEAP treated stallions after GnRH administrations (time 0) on d 21, relative to treatment. Stallions treated with pGnRH had a greater ($P<0.05$) response in concentrations of LH. Concentrations of FSH were similar between groups. Treatment with pGnRH tended to increase ($P<0.1$) the testosterone response to GnRH administration. Asterisks indicate differences ($P<0.05$) between means at individual time points.
Figure 8:
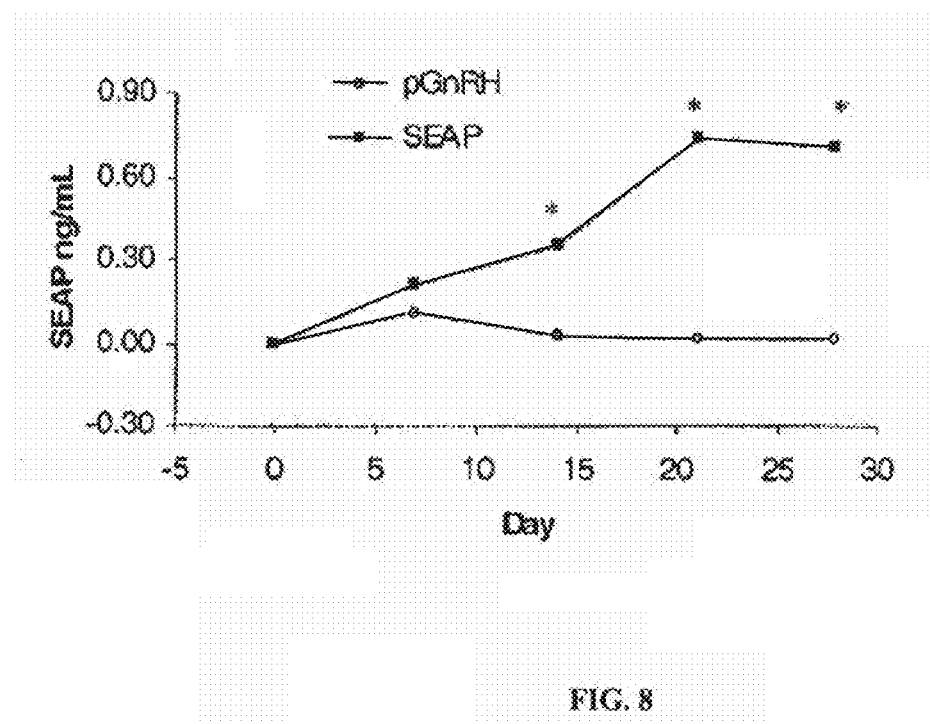
FIG. 8 displays a graph of plasma concentrations of SEAP in pGnRH and pSEAP treated stallions expressed as individual difference from pretreatment means. Treatment with pSEAP increased ($P<0.05$) plasma concentrations of SEAP. Asterisks indicate differences ($P<0.05$) between means at individual time points.
Figure 9:
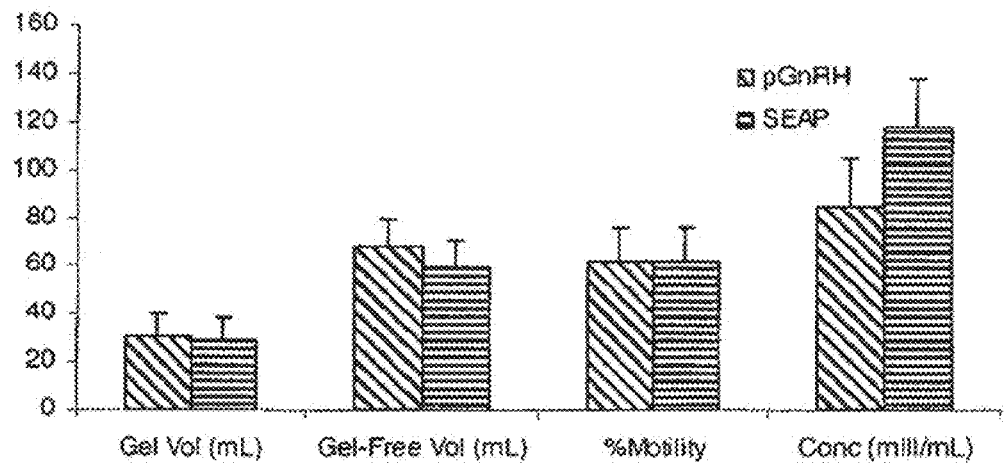
FIG. 9 displays bar graphs of seminal parameters from stallions treated with pGnRH or pSEAP evaluated on d 30 relative to treatment. Seminal characteristics evaluated were similar ($P>0.1$) between groups. Error bars indicate pooled standard error.
Figure 9:
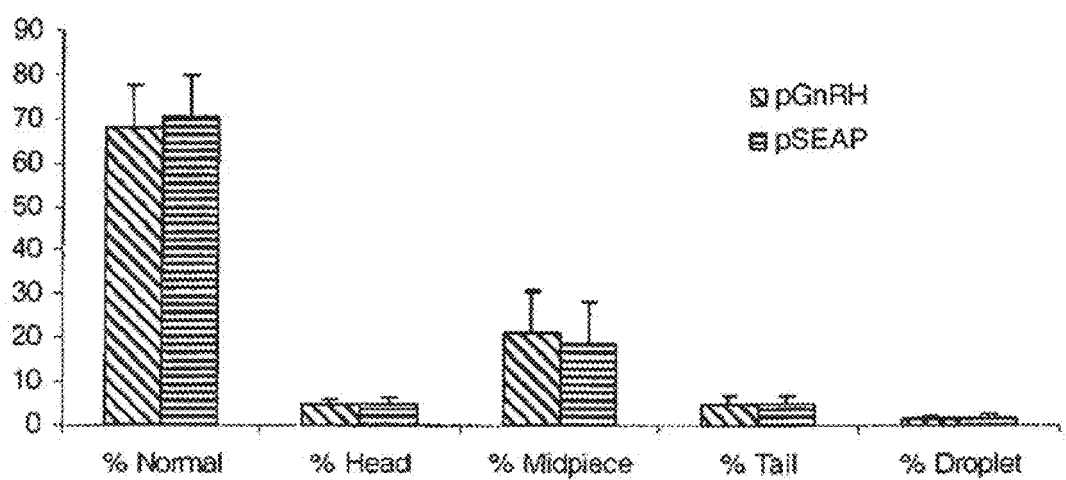

Tissue culture of SoI8 mouse myoblast cells transfected with pGnRH or no DNA indicated increased (P<0.01) expression in cells transfected with pGnRH (FIG. 5). The physiologic responses for the 2 mg and 4 mg DNA injection were similar in treated stallions; thus, the groups were combined and referred to collectively as "pGnRH-treated". Treatment with pGnRH increased (P<0.05) plasma concentrations of testosterone above controls in blood samples collected twice weekly by d 35 post treatment (FIG. 6C). The increase in testosterone concentrations from treated stallions was maintained for the duration of sample collection (d58). Plasma concentrations of LH and FSH in samples collected twice weekly were not different (P>0.1) between treatment groups (FIGS. 6A and 6B). Frequent blood sampling conducted around the GnRH challenge revealed an increased (P<0.01) response in plasma LH concentrations (FIG. 7A) and a tendency (P=0.0982) for increased response in testosterone concentrations (FIG. 7C). Conversely, concentrations of FSH were similar (P>0.1) between groups in response to the GnRH challenge (FIG. 7B). Control stallions responded to pSEAP with increased (P<0.01) plasma concentrations of SEAP (FIG. 8). Seminal characteristics did not differ (P>0.1) between groups (FIG. 9).

Example 6

Treatment of Stallions with GHRH and GnRH

Horse stallions are paired based on age and weight. Stallions are then randomly allotted so that each pair treatment is represented within each pair. Each stallion of a pair receives either intramuscular delivery of pGHRH and pGnRH (in a combination formulation) or pSEAP (negative control) by injection followed by electroporation (n=6/group). The plasmids are delivered as 4 mg of DNA in 2 mL WFI+0.1% LGS as described in Experiment 1. Blood samples are collected via jugular venipuncture into a heparinized tube on days 0, 1, 5, 8, 12, 15, 20, 22, 29, and twice weekly thereafter to day 58 relative to injection for assessment of GHRH, GnRH and SEAP concentrations. On day 22, all stallions receive indwelling jugular catheters for frequent blood sampling to characterize the GH secretory patterns of the two groups. Catheters are inserted at −60 min, and blood samples are collected into heparinized tubes at 0, 10, 20, 30, 45, 80, 90, 120, 150 min. Blood samples are immediately centrifuged (1,600×g at 5° C. for 15 min) and plasma is harvested and stored frozen (15° C.) until assay. Plasma samples are analyzed for SEAP by chemiluminescent assay (Phospha-Light System, Applied Biosystems, Bedford, Mass.). Concentrations of GH and IGF-I are determined by RIA as discussed in Example 4, above.

Concentrations of IGF-I are expected to increase but remain within the physiological range in treated stallions. Also expected is the elevation of SEAP concentrations in stallions treated with pSEAP but not in stallions receiving the GHRH and GnRH plasmids. The treated horses should also show increased plasma concentrations of testosterone above controls in blood samples collected twice weekly by d 35 post treatment. The increase in testosterone concentrations from treated stallions is expected to be maintained for the duration of sample collection (d 58). Plasma concentrations of LH and FSH in samples collected twice weekly should not be different between the treatment groups. Blood sampling conducted around the GnRH challenge is expected to reveal an increased response in plasma LH concentrations and increased response in testosterone concentrations. Conversely, concentrations of FSH are expected to be similar between groups in response to the GnRH challenge.

Previously, it was reported that stallions treated daily with recombinant equine GH had increased accessory sex gland function. In the present study, stallions are expected to exhibit an increased volume of gel. The decrease in number of sperm head abnormalities and gel-free volume reported should contrast from that previously reported. Sperm head abnormalities, in the present study, are analyzed using phase contrast imaging which is more sensitive to head abnormalities than the eosin-nigrosin stain used in the earlier study. The improved technique can detect abnormalities that were overlooked in the previous study. Also, the mean number of pre-treatment head abnormalities should be greater in the treated group.

The invention claimed is:

1. A pharmaceutical composition formulated for administration to a mammal in order to introduce to a cell of the mammal a GHRH product and a GnRH product, wherein the GHRH product comprises a nucleotide sequence that encodes GHRH and the GnRH product comprises a nucleotide sequence that encodes GnRH, and
wherein the nucleotide sequence that encodes GHRH is a plasmid having a nucleotide sequence as set forth in SEQ ID NO: 4 and the nucleotide sequence that encodes GnRH is a plasmid having a nucleotide sequence as set forth in SEQ ID NO: 1.

2. A kit comprising a first container comprising a nucleotide sequence that encodes GHRH and a second container comprising a nucleotide sequence that encodes GnRH, wherein the nucleotide sequence that encodes GHRH has a nucleotide sequence as set forth in SEQ ID NO: 4 and the nucleotide sequence that encodes GnRH has a nucleotide sequence as that set forth in SEQ ID NO: 1.

3. A method of enhancing fertility in a mammal in need thereof, the method comprising the step of administering to said mammal the pharmaceutical composition of claim 1.

4. The method according to claim 3, wherein the step of administering the pharmaceutical composition comprises injecting intramuscular, injecting intradermally, injecting intravenously, or delivering transdermally.

5. The method according to claim 3, further comprising the step of electroporating tissue of the mammal after the step of administering the pharmaceutical composition.

6. The method according to claim 5, comprising electroporating the tissue of the mammal using constant current.

7. The method according to claim 3, wherein the mammal is selected from the group consisting of: horses, dogs, cats, pigs, cows, sheep, goats, and primates.

8. The method according to claim 3, wherein the mammal exhibits enhanced fertility over an untreated mammal.

* * * * *

SEQUENCE LISTING

```
<160> NUMBER OF SEQ ID NOS: 10

<210> SEQ ID NO 1
<211> LENGTH: 2391
<212> TYPE: DNA
<213> ORGANISM: Artificial Sequence
<220> FEATURE:
<223> OTHER INFORMATION: Synthetic GnRH expression plasmid sequence or
      pGnRH

<400> SEQUENCE: 1
ccaccgcggt ggcggccgtc cgccctcggc accatcctca cgacacccaa atatggcgac      60
gggtgaggaa tggtggggag ttatttttag agcggtgagg aaggtgggca ggcagcaggt     120
gttggcgctc taaaataac tcccgggagt tattttaga gcggaggaat ggtggacacc      180
caaatatggc gacggttcct cacccgtcgc catatttggg tgtccgccct cggccggggc     240
cgcattcctg ggggccgggc ggtgctcccg cccgcctcga taaaaggctc cggggccggc     300
ggcggcccac gagctacccg gaggagcggg aggcgccaag cggatcccaa ggcccaactc     360
cccgaaccac tcagggtcct gtggacagct cacctagctg ccatggagcc aattccgaaa     420
cttctagccg gacttctgct gctgactctg tgtgtagtgg gctgctccag caaacactgg     480
tcctatggat tgcgccctgg ataatgaaag cttatcgggg tggcatccct gtgacccctc     540
cccagtgcct ctcctggccc tggaagttgc cactccagtg cccaccagcc ttgtcctaat     600
aaaattaagt tgcatcattt tgtctgacta ggtgtccttc tataatatta tggggtggag     660
gggggtggta tggagcaagg ggcaagttgg gaagacaacc tgtagggctc gaggggggggc     720 ccggtaccat gtgagcaaaa ggccagcaaa aggccaggaa ccgtaaaaag gccgcgttgc     780
tggcgttttt ccataggctc cgcccccctg acgagcatca caaaaatcga cgctcaagtc     840
agaggtggcg aaacccgaca ggactataaa gataccaggc gtttccccct ggaagctccc     900
tcgtgcgctc tcctgttccg accctgccgc ttaccggata cctgtccgcc tttctccctt     960
cgggaagcgt ggcgctttct catagctcac gctgtaggta tctcagttcg gtgtaggtcg    1020
ttcgctccaa gctgggctgt gtgcacgaac cccccgttca gcccgaccgc tgcgccttat    1080
ccggtaacta tcgtcttgag tccaacccgg taagacacga cttatcgcca ctggcagcag    1140
ccactggtaa caggattagc agagcgaggt atgtaggcgg tgctacagag ttcttgaagt    1200
ggtggcctaa ctacggctac actagaagaa cagtatttgg tatctgcgct ctgctgaagc    1260
cagttacctt cggaaaaaga gttggtagct cttgatccgg caaacaaacc accgctggta    1320
gcggtggttt ttttgtttac aagcagcaga ttacgcgcag aaaaaaagga tctcaagaag    1380
atcctttgat cttttctacg gggtctgacg ctcagctagc gctcagaaga actcgtcaag    1440
aaggcgatag aaggcgatgc gctgcgaatc gggagcggcg ataccgtaaa gcacgaggaa    1500
gcggtcagcc cattcgccgc caagctcttc agcaatatca cgggtagcca acgctatgtc    1560
```

```
ctgatagcgg tccgccacac ccagccggcc acagtcgatg aatccagaaa agcggccatt    1620
ttccaccatg atattcggca agcaggcatc gccatgagtc acgacgagat cctcgccgtc    1680
gggcatgcgc gccttgagcc tggcgaacag ttcggctggc gcgagcccct gatgctcttc    1740
gtccagatca tcctgatcga caagaccggc ttccatccga gtacgtgctc gctcgatgcg    1800
atgtttcgct tggtggtcga atgggcaggt agccggatca agcgtatgca gccgccgcat    1860
tgcatcagcc atgatggata ctttctcggc aggagcaagg tgagatgaca ggagatcctg    1920
ccccggcact tcgcccaata gcagccagtc ccttcccgct tcagtgacaa cgtcgagcac    1980
agctgcgcaa ggaacgcccg tcgtggccag ccacgatagc cgcgctgcct cgtcctgcag    2040
ttcattcagg gcaccggaca ggtcggtctt gacaaaaaga accgggcgcc cctgcgctga    2100
cagccggaac acggcggcat cagagcagcc gattgtctgt tgtgcccagt catagccgaa    2160
tagcctctcc acccaagcgg ccggagaacc tgcgtgcaat ccatcttgtt caatcatgcg    2220
aaacgatcct catcctgtct cttgatcaga tcttgatccc ctgcgccatc agatccttgg    2280
cggcaagaaa gccatccagt ttactttgca gggcttccca accttaccag agggcgcccc    2340
agctggcaat tccggttcgc ttgctgtcca taaaaccgcc cagtctgagc t             2391
```

```
<210> SEQ ID NO 2
<211> LENGTH: 113
<212> TYPE: DNA
<213> ORGANISM: Artificial Sequence
<220> FEATURE:
<223> OTHER INFORMATION: Synthetic porcine GnRH DNA sequence

<400> SEQUENCE: 2
ccatggagcc aattccgaaa cttctagccg gacttctgct gctgactctg tgtgtagtgg     60
gctgctccag caaacactgg tcctatggat gcgccctgg ataatgaaag ctt            113
```

```
<210> SEQ ID NO 3
<211> LENGTH: 33
<212> TYPE: PRT
<213> ORGANISM: Artificial Sequence
<220> FEATURE:
<223> OTHER INFORMATION: Snythetic porcine GnRH amino acid sequence

<400> SEQUENCE: 3

Met Glu Pro Ile Pro Lys Leu Leu Ala Gly Leu Leu Leu Thr Leu
1               5                   10                  15

Cys Val Val Gly Cys Ser Ser Gln His Trp Ser Tyr Gly Leu Arg Pro
            20                  25                  30
Gly
```

```
<210> SEQ ID NO 4
<211> LENGTH: 2505
<212> TYPE: DNA
<213> ORGANISM: Artificial Sequence
<220> FEATURE:
<223> OTHER INFORMATION: Synthetic nucleotide sequence pAV0242 or pGHRH

<400> SEQUENCE: 4
ccaccgcggt ggcggccgtc cgccctcggc accatcctca cgacacccaa atatggcgac     60
gggtgaggaa tggtggggag ttattttag agcggtgagg aaggtgggca ggcagcaggt    120
gttggcgctc taaaataac tcccgggagt tattttaga gcggaggaat ggtggacacc    180
caaatatggc gacggttcct cacccgtcgc catatttggg tgtccgccct cggcgggggc    240
cgcattcctg ggggccgggc ggtgctcccg cccgcctcga taaaaggctc cggggccggc    300
```

```
ggcggcccac gagctacccg gaggagcggg aggcgccaag cggatcccaa ggcccaactc      360
cccgaaccac tcagggtcct gtggacagct cacctagctg ccatggtgct ctgggtgttc      420
ttctttgtga tcctcaccct cagcaacagc tcccactgct ccccacctcc ccctttgacc      480
ctcaggatgc ggcggtatgc agatgccatc ttcaccaaca gctaccggaa ggtgctgggc      540
cagctgtccg cccgcaagct gctccaggac atcatgagca ggcagcaggg agagaggaac      600
caagagcaag gagcataatg aaagcttatc ggggtggcat ccctgtgacc cctccccagt      660
gcctctcctg gccctggaag ttgccactcc agtgcccacc agccttgtcc taataaaatt      720
aagttgcatc attttgtctg actaggtgtc cttctataat attatgggt ggagggggt       780 ggtatggagc aaggggcaag ttgggaagac aacctgtagg gctcgagggg gggcccggta      840
ccatgtgagc aaaaggccag caaaaggcca ggaaccgtaa aaaggccgcg ttgctggcgt      900
ttttccatag gctccgcccc cctgacgagc atcacaaaaa tcgacgctca agtcagaggt      960
ggcgaaaccc gacaggacta taaagatacc aggcgtttcc ccctggaagc tccctcgtgc     1020
gctctcctgt tccgaccctg ccgcttaccg gatacctgtc cgcctttctc ccttcgggaa     1080
gcgtggcgct ttctcatagc tcacgctgta ggtatctcag ttcggtgtag gtcgttcgct     1140
ccaagctggg ctgtgtgcac gaaccccccg ttcagcccga ccgctgcgcc ttatccggta     1200
actatcgtct tgagtccaac ccggtaagac acgacttatc gccactggca gcagccactg     1260
gtaacaggat tagcagagcg aggtatgtag gcggtgctac agagttcttg aagtggtggc     1320
ctaactacgg ctacactaga agaacagtat ttggtatctg cgctctgctg aagccagtta     1380
ccttcggaaa aagagttggt agctcttgat ccggcaaaca accaccgct ggtagcggtg      1440 gtttttttgt ttacaagcag cagattacgc gcagaaaaaa aggatctcaa gaagatcctt     1500
tgatcttttc tacgggtct gacgctcagc tagcgctcag aagaactcgt caagaaggcg      1560
atagaaggcg atgcgctgcg aatcgggagc ggcgatacog taaagcacga ggaagcggtc     1620
agcccattcg ccgccaagct cttcagcaat atcacgggta gccaacgcta tgtcctgata     1680
gcggtccgcc acacccagcc ggccacagtc gatgaatcca gaaaagcggc cattttccac     1740
catgatattc ggcaagcagg catcgccatg agtcacgacg agatcctcgc cgtcgggcat     1800
gcgcgccttg agcctggcga acagttcggc tggcgcgagc ccctgatgct cttcgtccag     1860
atcatcctga tcgacaagac cggcttccat ccgagtacgt gctcgctcga tgcgatgttt     1920
cgcttggtgg tcgaatgggc aggtagccgg atcaagcgta tgcagccgcc gcattgcatc     1980
agccatgatg gatactttct cggcaggagc aaggtgagat gacaggagat cctgccccgg     2040
cacttcgccc aatagcagcc agtcccttcc cgcttcagtg acaacgtcga gcacagctgc     2100
gcaaggaacg cccgtcgtgg ccagccacga tagccgcgct gcctcgtcct gcagttcatt     2160
cagggcaccg gacaggtcgg tcttgacaaa aagaaccggg cgcccctgcg ctgacagccg     2220
gaacacggcg gcatcagagc agccgattgt ctgttgtgcc cagtcatagc cgaatagcct     2280
ctccacccaa gcggccggag aacctgcgtg caatccatct tgttcaatca tgcgaaacga     2340
tcctcatcct gtctcttgat cagatcttga tccctgcgc catcagatcc ttggcggcaa      2400
gaaagccatc cagtttactt tgcagggctt cccaaccta ccagagggcg ccccagctgg      2460
caattccggt tcgcttgctg tccataaaac cgcccagtct gagct                     2505
```

<210> SEQ ID NO 5
<211> LENGTH: 40
<212> TYPE: PRT

```
<213> ORGANISM: Artificial Sequence
<220> FEATURE:
<223> OTHER INFORMATION: Synthetic Porcine GHRH amino acid sequence

<400> SEQUENCE: 5

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40

<210> SEQ ID NO 6
<211> LENGTH: 65
<212> TYPE: DNA
<213> ORGANISM: Artificial Sequence
<220> FEATURE:
<223> OTHER INFORMATION: DNA primer 1

<400> SEQUENCE: 6
ccatggagcc aattccgaaa cttctagccg gacttctgct gctgactctg tgtgtagtgg      60
gctgc                                                                 65

<210> SEQ ID NO 7
<211> LENGTH: 69
<212> TYPE: DNA
<213> ORGANISM: Artificial Sequence
<220> FEATURE:
<223> OTHER INFORMATION: DNA primer 2

<400> SEQUENCE: 7
aagctttcat tatccagggc gcaatccata ggaccagtgt tggctggagc agcccactac      60
acacagagt                                                             69

<210> SEQ ID NO 8
<211> LENGTH: 20
<212> TYPE: DNA
<213> ORGANISM: Artificial Sequence
<220> FEATURE:
<223> OTHER INFORMATION: DNA primer 3

<400> SEQUENCE: 8
ccatggagcc aattccgaaa                                                 20

<210> SEQ ID NO 9
<211> LENGTH: 21
<212> TYPE: DNA
<213> ORGANISM: Artificial Sequence
<220> FEATURE:
<223> OTHER INFORMATION: DNA primer 4

<400> SEQUENCE: 9
aagctttcat tatccagggc g                                               21

<210> SEQ ID NO 10
<211> LENGTH: 5019
<212> TYPE: DNA
<213> ORGANISM: Artificial Sequence
<220> FEATURE:
<223> OTHER INFORMATION: Synthetic SEAP-expressing plasmid: pAV5012
      C5-12 SEAP or pSEAP

<400> SEQUENCE: 10
gtaccgagct ccaccgcggt ggcggccgtc cgccctcggc accatcctca cgacacccaa      60
```

```
atatggcgac gggtgaggaa tggtggggag ttatttttag agcggtgagg aaggtgggca    120
ggcagcaggt gttggcgctc taaaaataac tcccgggagt tatttttaga gcggaggaat    180
ggtggacacc caaatatggc gacggttcct cacccgtcgc catatttggg tgtccgccct    240
cggccggggc cgcattcctg ggggccgggc ggtgctcccg cccgcctcga taaaaggctc    300
cggggccggc ggcggcccac gagctacccg gaggagcggg aggcgccaag ctctagaact    360
agtggatccc ccgggctgca ggaattcgat atcaagcttc gaatcgcgaa ttcgcccacc    420
atgctgctgc tgctgctgct gctgggcctg aggctacagc tctccctggg catcatccca    480
gttgaggagg agaacccgga cttctggaac cgcgaggcag ccgaggccct gggtgccgcc    540
aagaagctgc agcctgcaca gacagccgcc aagaacctca tcatcttcct gggcgatggg    600
atgggggtgt ctacggtgac agctgccagg atcctaaaag gcagaagaa ggacaaactg    660 gggcctgaga taccctggc catggaccgc ttcccatatg tggctctgtc aagacatac    720 aatgtagaca acatgtgcc agacagtgga gccacagcca cggcctacct gtgcggggtc    780
aagggcaact tccagaccat tggcttgagt gcagccgccc gctttaacca gtgcaacacg    840
acacgcggca acgaggtcat ctccgtgatg aatcggccca agaaagcagg gaagtcagtg    900
ggagtggtaa ccaccacacg agtgcagcac gcctcgccag ccggcaccta cgcccacacg    960
gtgaaccgca actggtactc ggacgccgac gtgcctgcct cggcccgcca ggaggggtgc   1020
caggacatcg ctacgcagct catctccaac atggacattg acgtgatcct aggtggaggc   1080
cgaaagtaca tgtttcgcat gggaaccca gaccctgagt acccagatga ctacagccaa   1140
ggtgggacca ggctggacgg gaagaatctg gtgcaggaat ggctggcgaa cgccagggt   1200 gcccggtatg tgtggaaccg cactgagctc atgcaggctt ccctggaccc gtctgtgacc   1260
catctcatgg gtctctttga gcctggagac atgaaatacg agatccaccg agactccaca   1320
ctggacccct ccctgatgga gatgacagag gctgccctgc gcctgctgag caggaacccc   1380
cgcggcttct tcctcttcgt ggagggtggt cgcatcgacc atggtcatca tgaaagcagg   1440
gcttaccggg cactgactga gacgatcatg ttcgacgacg ccattgagag ggcggggcag   1500
ctcaccagcg aggaggacac gctgagcctc gtcactgccg accactccca cgtcttctcc   1560
ttcggaggct acccctgcg agggagctcc atcttcgggc tggccctgg caaggccgg   1620 gacaggaagg cctacacggt cctcctatac ggaaacggtc caggctatgt gctcaaggac   1680
ggcgcccggc cggatgttac cgagagcgag agcgggagcc ccgagtatcg gcagcagtca   1740
gcagtgcccc tggacgaaga gacccacgca ggcgaggacg tggcggtgtt cgcgcgcggc   1800
ccgcaggcgc acctggttca cggcgtgcag gagcagacct tcatagcgca cgtcatggcc   1860
ttcgccgcct gctggagcc ctacaccgcc tgcgacctgg cgccccgc cggcaccacc   1920 gacgccgcgc acccgggtta ctctagagtc ggggcggccg ggcgcttcga gcagacatga   1980
taagatacat tgatgagttt ggacaaacca caactagaat gcagtgaaaa aaatgcttta   2040
tttgtgaaat ttgtgatgct attgctttat ttgtaaccat tataagctgc aataaacaag   2100
ttaacaacaa caattgcatt cattttatgt ttcaggttca gggggaggtg tgggaggttt   2160
tttaaagcaa gtaaacctc tacaaatgtg gtaaatcga taaggatccg tcgaccgatg   2220
cccttgagag ccttcaaccc agtcagctcc ttccggtggg cgcggggcat gactatcgtc   2280
gccgcactta tgactgtctt ctttatcatg caactcgtag acaggtgcc ggcagcgctc   2340 ttccgcttcc tcgctcactg actcgctgcg ctcggtcgtt cggctgcggc gagcggtatc   2400
```

```
agctcactca aaggcggtaa tacgttatc cacagaatca ggggataacg caggaaagaa    2460
catgtgagca aaaggccagc aaaaggccag gaaccgtaaa aaggccgcgt tgctggcgtt    2520
tttccatagg ctccgccccc ctgacgagca tcacaaaaat cgacgctcaa gtcagaggtg    2580
gcgaaacccg acaggactat aaagatacca ggcgtttccc cctggaagct ccctcgtgcg    2640
ctctcctgtt ccgaccctgc cgcttaccgg atacctgtcc gcctttctcc cttcgggaag    2700
cgtggcgctt tctcatagct cacgctgtag gtatctcagt tcggtgtagg tcgttcgctc    2760
caagctgggc tgtgtgcacg aaccccccgt tcagcccgac cgctgcgcct tatccggtaa    2820
ctatcgtctt gagtccaacc cggtaagaca cgacttatcg ccactggcag cagccactgg    2880
taacaggatt agcagagcga ggtatgtagg cggtgctaca gagttcttga agtggtggcc    2940
taactacggc tacactagaa ggacagtatt tggtatctgc gctctgctga agccagttac    3000
cttcggaaaa agagttggta gctcttgatc cggcaaacaa accaccgctg gtagcggtgg    3060
tttttttgtt tgcaagcagc agattacgcg cagaaaaaaa ggatctcaag aagatccttt    3120
gatcttttct acggggtctg acgctcagtg gaacgaaaac tcacgttaag ggattttggt    3180
catgagatta tcaaaaagga tcttcaccta gatcctttta aattaaaaat gaagttttaa    3240
atcaatctaa agtatatatg agtaaacttg gtctgacagt taccaatgct taatcagtga    3300
ggcacctatc tcagcgatct gtctatttcg ttcatccata gttgcctgac tccccgtcgt    3360
gtagataact acgatacggg agggcttacc atctggcccc agtgctgcaa tgataccgcg    3420
agacccacgc tcaccggctc cagatttatc agcaataaac cagccagccg aagggccga    3480 gcgcagaagt ggtcctgcaa ctttatccgc ctccatccag tctattaatt gttgccggga    3540
agctagagta agtagttcgc cagttaatag tttgcgcaac gttgttgcca ttgctacagg    3600
catcgtggtg tcacgctcgt cgtttggtat ggcttcattc agctccggtt cccaacgatc    3660
aaggcgagtt acatgatccc ccatgttgtg caaaaaagcg gttagctcct tcggtcctcc    3720
gatcgttgtc agaagtaagt tggccgcagt gttatcactc atggttatgg cagcactgca    3780
taattctctt actgtcatgc catccgtaag atgcttttct gtgactggtg agtactcaac    3840
caagtcattc tgagaatagt gtatgcggcg accgagttgc tcttgcccgg cgtcaatacg    3900
ggataatacc gcgccacata gcagaacttt aaaagtgctc atcattggaa aacgttcttc    3960
ggggcgaaaa ctctcaagga tcttaccgct gttgagatcc agttcgatgt aacccactcg    4020
tgcacccaac tgatcttcag catctttac tttcaccagc gtttctgggt gagcaaaaac    4080
aggaaggcaa aatgccgcaa aaaagggaat aagggcgaca cggaaatgtt gaatactcat    4140
actcttcctt tttcaatatt attgaagcat ttatcagggt tattgtctca tgagcggata    4200
catatttgaa tgtatttaga aaataaaca aatagggtt ccgcgcacat ttccccgaaa    4260
agtgccacct gacgcgccct gtagcggcgc attaagcgcg gcgggtgtgg tggttacgcg    4320
cagcgtgacc gctacacttg ccagcgccct agcgcccgct cctttcgctt tcttcccttc    4380
ctttctcgcc acgttcgccg gctttccccg tcaagctcta aatcggggc tccctttagg    4440 gttccgattt agtgctttac ggcacctcga cccaaaaaa cttgattagg gtgatggttc    4500
acgtagtggg ccatcgccct gatagacggt ttttcgccct tgacgttgg agtccacgtt    4560 ctttaatagt ggactcttgt tccaaactgg aacaacactc aaccctatct cggtctattc    4620
ttttgattta agggatttt tgccgatttc ggcctattgg ttaaaaaatg agctgattta    4680
acaaaaattt aacgcgaatt ttaacaaaat attaacgttt acaatttccc attcgccatt    4740
caggctgcgc aactgttggg aagggcgatc ggtgcgggcc tcttcgctat tacgccagcc    4800
```

```
caagctacca tgataagtaa gtaatattaa ggtacgggag gtacttggag cggccgcaat    4860
aaaatatctt tattttcatt acatctgtgt gttggttttt tgtgtgaatc gatagtacta    4920
acatacgctc tccatcaaaa caaaacgaaa caaaacaaac tagcaaaata ggctgtcccc    4980
agtgcaagtg caggtgccag aacatttctc tatcgatag                           5019
```